(12) United States Patent
Yokota et al.

(10) Patent No.: US 11,597,928 B2
(45) Date of Patent: Mar. 7, 2023

(54) NUCLEIC ACID COMPLEX

(71) Applicants: National University Corporation Tokyo Medical and Dental University, Tokyo (JP); Takeda Pharmaceutical Company Limited, Osaka (JP)

(72) Inventors: Takanori Yokota, Tokyo (JP); Tetsuya Nagata, Tokyo (JP); Hideki Furukawa, Kanagawa (JP); Yasuo Nakagawa, Kanagawa (JP); Takatoshi Yogo, Kanagawa (JP); Ryosuke Tokunoh, Kanagawa (JP); Shigekazu Sasaki, Kanagawa (JP); Kosuke Hidaka, Kanagawa (JP); Tomohiro Seki, Kanagawa (JP); Kenichi Miyata, Kanagawa (JP); Akio Uchida, Kanagawa (JP)

(73) Assignees: National University Corporation Tokyo Medical and Dental University, Tokyo (JP); Takeda Pharmaceutical Company Limited, Osaka (JP)

( * ) Notice: Subject to any disclaimer, the term of this patent is extended or adjusted under 35 U.S.C. 154(b) by 84 days.

(21) Appl. No.: 16/980,191

(22) PCT Filed: Mar. 13, 2019

(86) PCT No.: PCT/JP2019/010392
§ 371 (c)(1),
(2) Date: Sep. 11, 2020

(87) PCT Pub. No.: WO2019/177061
PCT Pub. Date: Sep. 19, 2019

(65) Prior Publication Data
US 2021/0024929 A1 Jan. 28, 2021

(30) Foreign Application Priority Data
Mar. 14, 2018 (JP) .............................. JP2018-047294

(51) Int. Cl.
C07H 21/04 (2006.01)
C12N 15/113 (2010.01)
A61P 25/00 (2006.01)

(52) U.S. Cl.
CPC ............ *C12N 15/113* (2013.01); *A61P 25/00* (2018.01); *C12N 2310/11* (2013.01); *C12N 2310/341* (2013.01)

(58) Field of Classification Search
None
See application file for complete search history.

(56) References Cited

U.S. PATENT DOCUMENTS

| 2011/0034545 A1 | 2/2011 | Kubo et al. |
| 2016/0130583 A1 | 5/2016 | Yokota et al. |
| 2016/0145614 A1 | 5/2016 | Yokota et al. |
| 2019/0247414 A1 | 8/2019 | Yokota et al. |

FOREIGN PATENT DOCUMENTS

| EP | 2 264 167 A1 | 12/2010 |
| JP | 2016-524588 A | 8/2016 |
| JP | 2016-526529 A | 9/2016 |
| WO | WO-2009/123185 A1 | 10/2009 |
| WO | WO-2011/008857 A1 | 1/2011 |
| WO | WO-2017/053999 A1 | 3/2017 |
| WO | WO-2018/056442 A1 | 3/2018 |

OTHER PUBLICATIONS

Hagedorn et al., "Locked nucleic acid: modality, diversity, and drug discovery," Drug Discovery Today, Jan. 2018, 23(1):101-114.
Qiagen, "Antisense LNA GapmeRs Handbook: LNA-optimized oligonucleotides for strand specific knockdown of mRNA and 1 ncRNA," Oct. 1, 2017, https://qiagen.com/us/resources/download.aspx?id=21372dc0-b345-4af1-8b00-b196068041a4&lang-en, 20 pages.
Supplementary European Search Report dated Feb. 1, 2022 in EP 19767189.
International Search Report dated Jun. 11, 2019, in PCT/JP2019/010392.

*Primary Examiner* — Kimberly Chong
(74) *Attorney, Agent, or Firm* — Foley & Lardner LLP

(57) ABSTRACT

Developed and provided is: a nucleic acid agent that is efficiently delivered to the central nervous system, to which drug delivery is inhibited by the blood brain barrier mechanism, and that provides an antisense effect to a target transcription product at the delivery site; and a composition containing such a nucleic acid agent.
Provided is a double-stranded nucleic acid complex consisting of a first nucleic acid strand and a second nucleic acid strand that are annealed to each other; wherein the first nucleic acid strand hybridizes with part of a target transcription product and has an antisense effect on the target transcription product; and wherein the second nucleic acid strand includes a base sequence complementary to the first nucleic acid strand and is conjugated to a phosphatidylethanolamine or an analog thereof.

20 Claims, 4 Drawing Sheets
Specification includes a Sequence Listing.

SEQUENCE LISTING

```
<160> NUMBER OF SEQ ID NOS: 8

<210> SEQ ID NO 1
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (14)..(15)
```

```
<223> OTHER INFORMATION: LNA
<220> FEATURE:
<221> NAME/KEY: misc_feature
<222> LOCATION: (1)..(1), (16)..(16)
<223> OTHER INFORMATION: 5-methylcytosine LNA

<400> SEQUENCE: 1
ctagttcact gaatgc                                                       16

<210> SEQ ID NO 2
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (14)..(16)
<223> OTHER INFORMATION: 2'-O-Me RNA

<400> SEQUENCE: 2
gcauucagug aacuag                                                       16

<210> SEQ ID NO 3
<211> LENGTH: 6982
<212> TYPE: DNA
<213> ORGANISM: Mus musculus
<220> FEATURE:
<223> OTHER INFORMATION: Malat1 non-coding RNA

<400> SEQUENCE: 3
aggcattcag gcagcgagag cagagcagcg tagagcagca cagctgagct cgtgaggcag        60
gagactcagc ccgaggaaat cgcagataag tttttaatta aaagattga gcagtaaaaa       120 gaattagaac tctaaactta agctaataga gtagcttatc gaaatattac ttagtcttaa       180
taatctaaga agatcttaag agataacatg aaggcttatt taaacagttt gaaaaaggaa       240
atgaggagaa aagtatttgt actgtataat ggaggctgac cagagcagtt taggagattg       300
taaagggagg ttttgtgaag ttctaaaagg ttctagtttg aaggtcggcc ttgtagatta       360
aaacgaaggt tacctaaata gaatctaagt ggcatttaaa acagtaaagt tgtagagaat       420
agtttgaaaa tgaggtgtag ttttaaaaga ttgagaaaag taggttaagt tgacggccgt       480
tataaaaatc cttcgactgg cgcatgtacg tttgaaggca tgagttggaa cagggaaga       540 tggaagtgtt aggctagccg ggcgatggtg gcgcacgcct ttaatcctag cacttgggag       600
gcagaggcag gcggatttct gagttcgagg ccagcctggt ctacagagtg agttccagga       660
cagccagggc tacacagaga aaccctgtct tgaaaaaaca aaaaggttag gctagtatttt      720 ggagaaagaa gattagaaaa tggaagtgaa agacgaagaa gacatacagg aaggtgaaga       780
aaaagctgtt agagaagata ggaaaataga agacaaagca tctttagaag acagaaaagg       840
tacttaaagg cacaggtagt aggaagccga agaatagaag atagaaagaa gcaagataga       900
aaaacaaaat ggaagttaag acaactttgg atgccagcat tcaagatagg caaagaagat       960
aagattgagg ccaaaaggtt ggataagata taaagtcaga aggaaattat ctttaaagcc      1020
ataagttcaa atttctgatg gagcgagcag tttagaagag tctttagaca gccacataca      1080
agattgaagc tagcaatcaa agctactagg actgaagtaa aaagttaagg cagaatgcct      1140
ttgaagagtt agaagaatat taaaagcctt aacttgtagc ttaattttgc ttgatgacaa      1200
aaggactttt gataacagtt tcaagattgt cagcattttg cattggactt gagctgaggt      1260
gcttttaaaa tcctaacgac tagcattggc agctgaccca ggtctacaca gaagtgcatt      1320
```

```
cagtgaacta ggaagacagg agcggcagac aggagtcccg aagccagttt ggtgaagcta   1380
ggaaggactg aggagccagc agcagcagtg catggtgaag atagcccagg aaagagtgcg   1440
gttcggtgga ggaagctagg aagaaggagc catacggatg tggtggtgaa gctgggaaag   1500
ggttccagga tggtggagcg agagcgagtt ggtgatgaag ctagctggcg gcttggcttg   1560
tcaactgcgc ggaggaggcg agcaggcatt gtggagagga tagatagcgg ctcctagacc   1620
agcatgccag tgtgcaagaa aggctgcagg gagagcatgc ggtgcggtaa cattccttga   1680
ggtcggcaac atggtggtgg ttttctgtaa cttggatggt aacttgttta ctttgtctta   1740
atagttatgg gggagttgta ggcttctgtg taaagagata tatctggggc tgtatgtagg   1800
cctttgcggg tgttgtaggt ttttcttttt cagggttatg tcctcttgca tcttgtcaga   1860
agcttttgag ggctgactgc caaggcccag aaagaagaat ggtagatggc aagttgtctt   1920
taaccgctca gaggggaatg aatggtagag ccagcacaac ctcccagttt tgtaagacgt   1980
tgtagtttga acagatgacc taccacaagc ctcactcctg tgtaggggag gtaattgggc   2040
aaagtgcttt tggggaatg ggggcaaaat atattttgag ttcttttccc cttaggtctg    2100
tctagaatcc taaaggcaga tgactcaagg gaaccagaaa aaaggaaatc cactctcagg   2160
ataagcagag ctcgccaggt ttacagtttg taggaagtag aggatggatg ctagctttca   2220
cactgagtgt ggaggagctg gccatggcgg aattgctggt agtttactct ttccccctcc   2280
cttaatgaga tttgtaaaat cctaaacact tttacttgaa atatttggga gtggtcttaa   2340
cagggaggag tgggtggggg aaacgttttt tttctaagat tttccacaga tgctatagtt   2400
gtgttgacac actgggttag agaaggcgtg tactgctatg ctgttggcac gacaccttca   2460
gggactggag ctgccttttg tccttggaag agttttccca gttgccgctg aagtcagcac   2520
agtgcggctt tggttcacag tcacctcagg agaacctcag gagcttggct aggccagagg   2580
ttgaagttaa gttttacagc accgtgattt aaaatatttc attaaagggg aggggtaaaa   2640
cttagttggc tgtggccttg tgtttgggtg ggtgggggtg ttaggtaatt gtttagttta   2700
tgatttcaga taatcatacc agagaactta aatatttgga aaaacaggaa atctcagctt   2760
tcaagttggc aagtaactcc caatccagtt tttgcttctt ttttcctttt tctttttttg   2820
aggcgggcag ctaaggaagg ttggttcctc tgccggtccc tcgaaagcgt agggcttggg   2880
ggttggtctg gtccactggg atgatgtgat gctacagtgg ggactcttct gaagctgttg   2940
gatgaatata gattgtagtg tgtggttctc ttttgaaatt ttttcaggt gacttaatgt    3000 atcttaataa ctactatagg aacaaaggaa gtggctttaa tgaccctgaa ggaatttct    3060 ctggtgatag cttttatatt atcaagtaag agatactatc tcagttttgt ataagcaagt   3120 cttttttccta gtgtaggaga aatgattttc cttgtgacta aacaagatgt aaaggtatgc   3180 ttttttttctt cttgtgcatt gtatacttgt gtttatttgt aacttataat ttaagaatta   3240
tgataattca gcctgaatgt cttttagagg gtgggctttt gttgatgagg gaggggaaac   3300
cttttttttt ctgtagacct ttttcagata acaccatctg agtcataacc agcctggcag   3360
tgtgatgacg tagatgcaga gggagcagct ccttggtgaa tgagtgataa gtaaaggcag   3420
aaaaaataat gtcatgtctc catggggaat gagcatgagc cagagattgt tcctactgat   3480
gaaaagctgc atatgcaaaa atttaagcaa atgaaagcaa ccagtataaa gttatggcaa   3540
tacctttaaa agttatggct tatctaccaa gctttatcca caaaagtaaa gaattgatga   3600
aaaacagtga agatcaaatg ttcatctcaa aactgctttt acaaaagcag aatagaaatg   3660
```

-continued

```
aagtgaaaat gctgcattaa gcctggagta aaaagaagct gagcttgttg agatgagtgg    3720
gatcgagcgg ctgcgaggcg gtgcagtgtg ccaatgtttc gtttgcctca gacaggtttc    3780
tcttcataag cagaagagtt gcttcattcc atctcggagc aggaaacagc agactgctgt    3840
tgacagataa gtgtaacttg gatctgcagt attgcatgtt agggatagat aagtgccttt    3900
tttctctttt tccaaaaaga cctgtagagc tgttgaatgt ttgcagctgg cccctcttag    3960
gcagttcaga attttgagta gttttcccat ccagcctctt aaaaattcct aagccttgca    4020
ccgatgggct ttcatgatgg gatagctaat aggcttttgc atcgtaaact tcaacacaaa    4080
agcctacatg attaatgcct actttaatta cattgcttac aagattaagg aatctttatc    4140
ttgaagaccc catgaaaggg atcattatgt gctgaaaatt agatgttcat attgctaaaa    4200
tttaaatgtg ctccaatgta cttgtgctta aaatcattaa attatacaaa ttaataaaat    4260
acttcactag agaatgtatg tatttagaag gctgtctcct tatttaaata aagtcttgtt    4320
tgttgtctgt agttagtgtg ggcaattttg gggggatgtt cttctctaat cttttcagaa    4380
acttgacttc gaacacttaa gtggaccaga tcaggatttg agccagaaga ccgaaattaa    4440
ctttaaggca ggaaagacaa attttattct ccatgcagtg atgagcattt ataattgca    4500
ggcctggcat agaggccgtc taactaagga ctaagtacct taggcaggtg ggagatgatg    4560
gtcagagtaa aagtaacta catattttgt ttccagaaag tcaggggtct aatttgacca    4620
tggctaaaca tctagggtaa gacacttttc ccccacattt ccaaatatgc atgttgagtt    4680
taaatgctta cgatcatctc atccacttta gccttttgtc acctcacttg agccacgagt    4740
ggggtcaggc atgtgggttt aaagagtttt cctttgcaga gcctcatttc atccttcatg    4800
gagctgctca ggactttgca tataagcgct tgcctctgtc ttctgttctg ctagtgagtg    4860
tgtgatgtga gaccttgcag tgagtttgtt tttcctggaa tgtggaggga ggggggatg    4920
gggcttactt gttctagctt tttttttaca gaccacacag aatgcaggtg tcttgacttc    4980
aggtcatgtc tgttctttgg caagtaatat gtgcagtact gttccaatct gctgctatta    5040
gaatgcattg tgacgcgact ggagtatgat taaagaaagt tgtgtttccc caagtgtttg    5100
gagtagtggt tgttggagga aaagccatga gtaacaggct gagtgttgag gaaatggctc    5160
tctgcagctt taagtaaccc gtgtttgtga ttggagccga gtcccttttgc tgtgctgcct    5220
taggtaaatg ttttttgttca tttctggtga ggggggttgg gagcactgaa gcctttagtc    5280
tcttccagat tcaacttaaa atctgacaag aaataaatca gacaagcaac attcttgaag    5340
aaattttaac tggcaagtgg aaatgttttg aacagttccg tggtctttag tgcattatct    5400
ttgtgtaggt gttctctctc ccctcccttg gtcttaattc ttacatgcag gaacattgac    5460
aacagcagac atctatctat tcaaggggcc agagaatcca gacccagtaa ggaaaaatag    5520
cccatttact ttaaatcgat aagtgaagca gacatgccat tttcagtgtg gggattggga    5580
agccctagtt ctttcagatg tacttcagac tgtagaagga gcttccagtt gaattgaaat    5640
tcaccagtgg acaaaatgag gacaacaggt gaacgagcct tttcttgttt aagattagct    5700
actggtaatc tagtgttgaa tcctctccag cttcatgctg gagcagctag catgtgatgt    5760
aatgttggcc ttggggtgga ggggtgaggt gggcgctaag ccttttttta agattttca    5820
ggtaccctc actaaaggca ctgaaggctt aatgtaggac agcggagcct tcctgtgtgg    5880
caagaatcaa gcaagcagta ttgtatcgag accaaagtgg tatcatggtc ggttttgatt    5940
agcagtgggg actaccctac cgtaacacct tgttggaatt gaagcatcca aagaaaatac    6000
ttgagaggcc ctgggcttgt tttaacatct ggaaaaaagg ctgttttttat agcagcggtt    6060
```

```
accagcccaa acctcaagtt gtgcttgcag gggagggaaa aggggggaaag cgggcaacca    6120 gtttccccag cttttccaga atcctgttac aaggtctccc cacaagtgat ttctctgcca    6180
catcgccacc atgggccttt ggcctaatca cagacccttc accctcacc ttgatgcagc     6240 cagtagctgg atccttgagg tcacgttgca tatcggtttc aaggtaacca tggtgccaag    6300
gtcctgtggg ttgcaccaga aaaggccatc aatttccccc ttgcctgtaa tttaacatta    6360
aaaccatagc taagatgttt tatacatagc acctatgcag agtaaacaaa ccagtatggg    6420
tatagtatgt ttgataccag tgctgggtgg gaatgtagga agtcggatga aaagcaagcc    6480
tttgtaggaa gttgttgggg tgggattgca aaaattctct gctaagactt tttcaggtgg    6540
acataacaga cttggccaag ctagcatctt agtggaagca gattcgtcag tagggttgta    6600
aaggtttttc ttttcctgag aaaacaacct tttgttttct caggttttgc ttttggcct    6660 ttccctagct ttaaaaaaaa aaaagcaaaa gacgctggtg gctggcactc ctggtttcca    6720
ggacggggtt caagtccctg cggtgtcttt gcttgactct tatatcatga ggccattaca    6780 ttttcttgg agggttctaa aggctctggg tatggtagct gatatcactg gaacactccc     6840
cagcctcagt gttgaactct tgataattaa ctgcattgtc tttcaggtta tgcccaattc    6900
gtcttattac ctctgagtcg acacacctcc tactatttat tgaatacttt gattttatga    6960
aataaaaact aaatatctct ca                                             6982

<210> SEQ ID NO 4
<211> LENGTH: 8758
<212> TYPE: DNA
<213> ORGANISM: Homo sapiens
<220> FEATURE:
<223> OTHER INFORMATION: Malat1 non-coding RNA

<400> SEQUENCE: 4
gtaaaggact ggggccccgc aactggcctc tcctgccctc ttaagcgcag cgccatttta     60
gcaacgcaga agcccggcgc cgggaagcct cagctcgcct gaaggcaggt ccctctgac    120 gcctccggga gcccaggttt cccagagtcc ttgggacgca gcgacgagtt gtgctgctat   180
cttagctgtc cttataggct ggccattcca ggtggtggta tttagataaa accactcaaa   240
ctctgcagtt tggtcttggg gtttggagga aagcttttat ttttcttcct gctccggttc   300
agaaggtctg aagctcatac ctaaccaggc ataacacaga atctgcaaaa caaaaacccc   360 taaaaagca gacccagagc agtgtaaaca cttctgggtg tgtccctgac tggctgccca    420
aggtctctgt gtcttcggag acaaagccat tcgcttagtt ggtctacttt aaaaggccac   480
ttgaactcgc tttccatggc gatttgcctt gtgagcactt tcaggagagc ctggaagctg   540
aaaaacggta gaaaaatttc cgtgcgggcc gtgggggct ggcggcaact gggggccgc     600 agatcagagt gggccactgg cagccaacgg cccccggggc tcaggcgggg agcagctctg   660
tggtgtggga ttgaggcgtt ttccaagagt gggttttcac gtttctaaga tttcccaagc   720
agacagcccg tgctgctccg atttctcgaa caaaaaagca aaacgtgtgg ctgtcttggg   780
agcaagtcgc aggactgcaa gcagttgggg gagaaagtcc gccattttgc cacttctcaa   840
ccgtccctgc aaggctgggg ctcagttgcg taatggaaag taaagccctg aactatcaca   900
ctttaatctt ccttcaaaag gtggtaaact atacctactg tccctcaaga gaacacaaga   960
agtgctttaa gaggtatttt aaaagttccg gggttttgt gaggtgtttg atgacccgtt   1020
taaaatatga tttccatgtt tcttttgtct aaagtttgca gctcaaatct ttccacacgc   1080
```

```
tagtaattta agtatttctg catgtgtagt ttgcattcaa gttccataag ctgttaagaa    1140
aaatctagaa aagtaaaact agaacctatt tttaaccgaa gaactacttt ttgcctccct    1200
cacaaaggcg gcggaaggtg atcgaattcc ggtgatgcga gttgttctcc gtctataaat    1260
acgcctcgcc cgagctgtgc ggtaggcatt gaggcagcca gcgcaggggc ttctgctgag    1320
ggggcaggcg gagcttgagg aaaccgcaga taagtttttt tctctttgaa agatagagat    1380
taatacaact acttaaaaaa tatagtcaat aggttactaa gatattgctt agcgttaagt    1440
ttttaacgta attttaatag cttaagattt taagagaaaa tatgaagact tagaagagta    1500
gcatgaggaa ggaaaagata aaaggtttct aaaacatgac ggaggttgag atgaagcttc    1560
ttcatggagt aaaaaatgta tttaaaagaa aattgagaga aaggactaca gagccccgaa    1620
ttaataccaa tagaagggca atgcttttag attaaaatga aggtgactta aacagcttaa    1680
agtttagttt aaaagttgta ggtgattaaa ataatttgaa ggcgatcttt taaaaagaga    1740
ttaaaccgaa ggtgattaaa agaccttgaa atccatgacg cagggagaat tgcgtcattt    1800
aaagcctagt taacgcattt actaaacgca gacgaaaatg gaaagattaa ttgggagtgg    1860
taggatgaaa caatttggag aagatagaag tttgaagtgg aaaactggaa gacagaagta    1920
cgggaaggcg aagaaaagaa tagagaagat agggaaatta gaagataaaa acatactttt    1980
agaagaaaaa agataaattt aaacctgaaa agtaggaagc agaagaaaaa agacaagcta    2040
ggaaacaaaa agctaagggc aaaatgtaca aacttagaag aaaattggaa gatagaaaca    2100
agatagaaaa tgaaaatatt gtcaagagtt tcagatagaa aatgaaaaac aagctaagac    2160
aagtattgga gaagtataga agatagaaaa atataaagcc aaaaattgga taaaatagca    2220
ctgaaaaaat gaggaaatta ttggtaacca atttattttta aaagcccatc aatttaattt    2280
ctggtggtgc agaagttaga aggtaaagct tgagaagatg agggtgttta cgtagaccag    2340
aaccaattta gaagaatact tgaagctaga aggggaagtt ggttaaaaat cacatcaaaa    2400
agctactaaa aggactggtg taatttaaaa aaaactaagg cagaaggctt ttggaagagt    2460
tagaagaatt tggaaggcct taaatatagt agcttagttt gaaaaatgtg aaggactttc    2520
gtaacggaag taattcaaga tcaagagtaa ttaccaactt aatgttttg cattggactt     2580 tgagttaaga ttatttttta aatcctgagg actagcatta attgacagct gacccaggtg    2640
ctacacagaa gtggattcag tgaatctagg aagacagcag cagacaggat tccaggaacc    2700
agtgtttgat gaagctagga ctgaggagca agcgagcaag cagcagttcg tggtgaagat    2760
aggaaaagag tccaggagcc agtgcgattt ggtgaaggaa gctaggaaga aggaaggagc    2820
gctaacgatt tggtggtgaa gctaggaaaa aggattccag gaaggagcga gtgcaatttg    2880
gtgatgaagg tagcaggcgg cttggcttgg caaccacacg gaggaggcga gcaggcgttg    2940
tgcgtagagg atcctagacc agcatgccag tgtgccaagg ccacagggaa agcgagtggt    3000
tggtaaaaat ccgtgaggtc ggcaatatgt tgtttttctg gaacttactt atggtaacct    3060
tttatttatt ttctaatata atgggggagt ttcgtactga ggtgtaaagg gatttatatg    3120
gggacgtagg ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt ttttttttta cacgaatttg aggaaaacca aatgaatttg atagccaaat    3300
tgagacaatt tcagcaaatc tgtaagcagt ttgtatgttt agttggggta atgaagtatt    3360
tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
```

```
gggggcaaaa tatgttttca gttcttttc ccttaggtct gtctagaatc ctaaaggcaa    3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt ttccccccac cccttaatc agactttaaa    3720 agtgcttaac cccttaaact tgttattttt tacttgaagc attttgggat ggtcttaaca    3780
gggaagagaa agggtggggg agaaaatgtt tttttctaag attttccaca gatgctatag    3840
tactattgac aaactgggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080 gggagggca atattggca attagttggc agtggcctgt tacggttggg attggtgggg    4140
tgggtttagg taattgttta gtttatgatt gcagataaac tcatgccaga gaacttaaag    4200
tcttagaatg gaaaagtaa agaaatatca acttccaagt tggcaagtaa ctcccaatga    4260 tttagtttt tccccccag tttgaattgg gaagctgggg gaagttaaat atgagccact    4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt tttttcaggt gatttaataa taatttaaaa ctactataga    4560
aactgcagag caaaggaagt ggcttaatga tcctgaaggg atttcttctg atggtagctt    4620
ttgtattatc aagtaagatt ctattttcag ttgtgtgtaa gcaagttttt ttttagtgta    4680
ggagaaatac ttttccattg tttaactgca aaacaagatg ttaaggtatg cttcaaaaat    4740
tttgtaaatt gtttatttta aacttatctg tttgtaaatt gtaactgatt aagaattgtg    4800
atagttcagc ttgaatgtct cttagagggt gggcttttgt tgatgaggga ggggaaactt    4860 ttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaaattt taagcaaatg aaagctacca atttaaagtt    5100
acggaatcta ccatttttaaa gttaattgct tgtcaagcta taaccacaaa aataatgaat    5160
tgatgagaaa tacaatgaag aggcaatgtc catctcaaaa tactgctttt acaaaagcag    5220
aataaaagcg aaaagaaatg aaaatgttac actacattaa tcctggaata aaagaagccg    5280
aaataaatga gagatgagtt gggatcaagt ggattgagga ggctgtgctg tgtgccaatg    5340
tttcgtttgc ctcagacagg tatctcttcg ttatcagaag agttgcttca tttcatctgg    5400
gagcagaaaa cagcaggcag ctgttaacag ataagtttaa cttgcatctg cagtattgca    5460
tgttagggat aagtgcttat ttttaagagc tgtggagttc ttaaatatca accatggcac    5520
tttctcctga ccccttccct aggggatttc aggattgaga aatttttcca tcgagccttt    5580
ttaaaattgt aggacttgtt cctgtgggct tcagtgatgg gatagtacac ttcactcaga    5640
ggcatttgca tctttaaata atttcttaaa agcctctaaa gtgatcagtg ccttgatgcc    5700
aactaaggaa atttgtttag cattgaatct ctgaaggctc tatgaaagga atagcatgat    5760
gtgctgttag aatcagatgt tactgctaaa atttacatgt tgtgatgtaa attgtgtaga    5820
```

```
aaaccattaa atcattcaaa ataataaact attttttatta gagaatgtat acttttagaa    5880
agctgtctcc ttatttaaat aaaatagtgt ttgtctgtag ttcagtgttg gggcaatctt    5940 ggggggatt cttctctaat cttcagaaa ctttgtctgc gaacactctt taatggacca     6000
gatcaggatt tgagcggaag aacgaatgta actttaaggc aggaaagaca aattttattc    6060
ttcataaagt gatgagcata taataattcc aggcacatgg caatagaggc cctctaaata    6120
aggaataaat aacctcttag acaggtggga gattatgatc agagtaaaag gtaattacac    6180
attttatttc cagaaagtca ggggtctata aattgacagt gattagagta atacttttc     6240 acattccaa agtttgcatg ttaactttaa atgcttacaa tcttagagtg gtaggcaatg    6300
ttttacacta ttgaccttat atagggaagg agggggtgc ctgtgggtt ttaaagaatt     6360 ttcctttgca gaggcatttc atccttcatg aagccattca ggattttgaa ttgcatatga    6420
gtgcttggct cttccttctg ttctagtgag tgtatgagac cttgcagtga gtttatcagc    6480
atactcaaaa ttttttcct ggaatttgga gggatgggag gaggggtgg ggcttacttg      6540 ttgtagcttt tttttttt acagacttca cagagaatgc agttgtcttg acttcaggtc     6600
tgtctgttct gttggcaagt aaatgcagta ctgttctgat cccgctgcta ttagaatgca    6660
ttgtgaaacg actggagtat gattaaaagt tgtgttcccc aatgcttgga gtagtgattg    6720
ttgaaggaaa aaatccagct gagtgataaa ggctgagtgt tgaggaaatt tctgcagttt    6780
taagcagtcg tatttgtgat tgaagctgag tacattttgc tggtgtattt ttaggtaaaa    6840 tgcttttgt tcatttctgg tggtgggagg ggactgaagc ctttagtctt ttccagatgc     6900
aaccttaaaa tcagtgacaa gaaacattcc aaacaagcaa cagtcttcaa gaaattaaac    6960
tggcaagtgg aaatgtttaa acagttcagt gatctttagt gcattgttta tgtgtgggtt    7020
tctctctccc ctcccttggt cttaattctt acatgcagga acactcagca gacacacgta    7080
tgcgaagggc cagagaagcc agacccagta agaaaaaata gcctatttac tttaaataaa    7140
ccaaacattc catttaaat gtggggattg ggaaccacta gttctttcag atggtattct    7200
tcagactata gaaggagctt ccagttgaat tcaccagtgg acaaaatgag gaaaacaggt    7260
gaacaagctt tttctgtatt tacatacaaa gtcagatcag ttatgggaca atagtattga    7320
atagatttca gctttatgct ggagtaactg gcatgtgagc aaactgtgtt ggcgtggggg    7380
tggaggggtg aggtgggcgc taagcctttt tttaagattt ttcaggtacc cctcactaaa    7440
ggcaccgaag gcttaaagta ggacaaccat ggagccttcc tgtggcagga gagacaacaa    7500
agcgctatta tcctaaggtc aagagaagtg tcagcctcac ctgattttta ttagtaatga    7560
ggacttgcct caactccctc tttctggagt gaagcatccg aaggaatgct tgaagtaccc    7620
ctgggcttct cttaacattt aagcaagctg tttttatagc agctcttaat aataaagccc    7680
aaatctcaag cggtgcttga aggggaggga aaggggaaa gcgggcaacc acttttccct    7740
agcttttcca gaagcctgtt aaaagcaagg tctccccaca agcaacttct ctgccacatc    7800
gccaccccgt gcctttgat ctagcacaga cccttcaccc ctcacctcga tgcagccagt     7860
agcttggatc cttgtgggca tgatccataa tcggtttcaa ggtaacgatg gtgtcgaggt    7920
ctttggtggg ttgaactatg ttagaaaagg ccattaattt gcctgcaaat tgttaacaga    7980
agggtattaa aaccacagct aagtagctct attataatac ttatccagtg actaaaacca    8040 acttaaaccca gtaagtggag aaataacatg ttcaagaact gtaatgctgg gtgggaacat   8100
gtaacttgta gactggagaa gataggcatt tgagtggctg agagggcttt tgggtgggaa    8160
tgcaaaaatt ctctgctaag acttttcag gtgaacataa cagacttggc caagctagca    8220
```

```
tcttagcgga agctgatctc caatgctctt cagtagggtc atgaaggttt ttcttttcct    8280
gagaaaacaa cacgtattgt tttctcaggt tttgcttttt ggccttttc tagcttaaaa    8340 aaaaaaaaag caaagatgc tggtggttgg cactcctggt ttccaggacg gggttcaaat    8400
ccctgcggcg tctttgcttt gactactaat ctgtcttcag gactctttct gtatttctcc    8460
ttttctctgc aggtgctagt tcttggagtt ttggggaggt gggaggtaac agcacaatat    8520 cttgaacta tatacatcct tgatgtataa tttgtcagga gcttgacttg attgtatatt    8580
catatttaca cgagaaccta atataactgc cttgtctttt tcaggtaata gcctgcagct    8640
ggtgttttga aagccctac tgctgaaaac ttaacaattt tgtgtaataa aaatggagaa    8700
gctctaaatt gttgtggttc ttttgtgaat aaaaaaatct tgattgggga aaaaaaa      8758
```

<210> SEQ ID NO 5
<211> LENGTH: 2534
<212> TYPE: DNA
<213> ORGANISM: Mus musculus
<220> FEATURE:
<223> OTHER INFORMATION: SR-B1 mRNA

<400> SEQUENCE: 5

```
ggaatcccgc gccgaactcg ggggcgggct gcccgggcca tggcgcataa agcctctggc      60
cacctgcagg gctactgctg ctccggccac cgccaggcac acaccttgct gctgagggag     120
tctcggcttc tgtcatctct gtggcctccg tcacctctgt ctccgtctcc ttcaggtcct     180
gagccccgag agccccttcc gcgcacgcgg acatgggcgg cagctccagg gcgcgctggg     240
tggccttggg gttgggcgcc ctggggctgc tgtttgctgc gctcggcgtt gtcatgatcc     300
tcatggtgcc ctccctcatc aagcagcagg tgctcaagaa tgtccgcata gacccgagca     360
gcctgtcctt cgggatgtgg aaggagatcc ccgtcccttt ctacttgtct gtctacttct     420
tcgaagtggt caacccaaac gaggtcctca acggccagaa gccagtagtc cgggagcgtg     480
gaccctatgt ctacagggag ttcagacaaa aggtcaacat caccttcaat gacaacgaca     540
ccgtgtcctt cgtggagaac cgcagcctcc atttccagcc tgacaagtcg catggctcag     600
agagtgacta cattgtactg cctaacatct tggtcctggg gggctcgata ttgatggaga     660
gcaagcctgt gagcctgaag ctgatgatga ccttggcgct ggtcaccatg ggccagcgtg     720 ctttttatgaa ccgcacagtt ggtgagatcc tgtgggcta tgacgatccc ttcgtgcatt     780
ttctcaacac gtacctccca gacatgcttc ccataaaggg caaatttggc ctgtttgttg     840
ggatgaacaa ctcgaattct ggggtcttca ctgtcttcac gggcgtccag aatttcagca     900
ggatccatct ggtggacaaa tggaacggac tcagcaagat cgattattgg cattcagagc     960
agtgtaacat gatcaatggg acttccggca agatgtgggc cccttcatg acacccgaat    1020 cctcgctgga attcttcagc ccggaggcat gcaggtccat gaagctgacc tacaacgaat    1080
caagggtgtt tgaaggcatt ccacgtatc gcttcacggc cccgatact ctgtttgcca     1140 acgggtccgt ctacccaccc aacgaaggct ctgcccatg ccgagagtct ggcattcaga    1200
atgtcagcac ctgcaggttt ggtgcgcctc tgtttctctc ccaccccac ttttacaacg    1260 ccgaccctgt gttgtcagaa gctgttcttg gtctgaaccc taacccaaag gagcattcct    1320
tgttcctaga catccatccg gtcactggga tccccatgaa ctgttctgtg aagatgcagc    1380
tgagcctcta catcaaatct gtcaagggca tcgggcaaac agggaagatc gagccagtag    1440
ttctgccgtt gctgtggttc gaacagagcg gagcaatggg tggcaagccc ctgagcacgt    1500
```

```
tctacacgca gctggtgctg atgccccagg ttcttcacta cgcgcagtat gtgctgctgg    1560
ggcttggagg cctcctgttg ctggtgccca tcatctgcca actgcgcagc caggagaaat    1620 gcttttgtt ttggagtggt agtaaaaagg ctcccagga taaggaggcc attcaggcct      1680
actctgagtc cctgatgtca ccagctgcca agggcacggt gctgcaagaa gccaagctat    1740
agggtcctga agacactata agcccccccaa acctgatagc ttggtcagac cagccaccca   1800
gtccctacac cccgcttctt gaggactctc tcagcggaca gcccaccagt gccatggcct    1860
gagcccccag atgtcacacc tgtccgcacg cacggcacat ggatgcccac gcatgtgcaa    1920
aaacaactca gggaccaggg acagacctgc tgccaagtga gcctgatggg ccacaggtgt    1980
gctcttctaa atggcctgtg agccaggctg tgggaactct agctgctgtc agcccctcct    2040
gtaggagctg gccctgccca ggctcctgac ttccctcagg aagtctttct gtctttctcc    2100
atcagtctga aagccttagt tcccacagag gacggatctg tcactcctag ggctgggca    2160 tatgtcggcc tcttgtgcca aggccaggca agcagctcca ggtcctgacc agtttgcaca    2220
cacactctgg agctgtatct ggcgcttttt ctatcgtctc tgctatgtca ctgaattaac    2280
cactgtacgt ggcagaggtg gcaggcccct cagggtcctt attttcagg catggggtca    2340 aagctagagg tatgggccgt ctacacccc ccgcccccg gcatctagtg tacctcacca     2400
gagggtattc ggaggcccag catcctgcaa ccgacccctt ttttctactg gaagagaaat    2460
tttatcatct tttgaaagga agtcatgact gaagcaataa accttttcac tgattcaaca    2520
aaaaaaaaaa aaaa                                                      2534

<210> SEQ ID NO 6
<211> LENGTH: 2759
<212> TYPE: DNA
<213> ORGANISM: Homo sapiens
<220> FEATURE:
<223> OTHER INFORMATION: SR-B1 mRNA

<400> SEQUENCE: 6
gctcaggccc cgcccctgcc gccggaatcc tgaagcccaa ggctgccgg gggcggtccg      60 gcggcgccgg cgatggggca taaaaccact ggccacctgc cgggctgctc ctgcgtgcgc    120
tgccgtcccg gatccaccgt gcctctgcgg cctgcgtgcc cggagtcccc gcctgtgtcg    180
tctctgtcgc cgtccccgtc tcctgccagg gcggagccc tgcgagccgc gggtgggccc     240
caggcgcgca gacatgggct gctccgccaa agcgcgctgg gctgccgggg cgctgggcgt    300
cgcggggcta ctgtgcgctg tgctgggcgc tgtcatgatc gtgatggtgc cgtcgctcat    360
caagcagcag gtccttaaga cgtgcgcat cgaccccagt agcctgtcct tcaacatgtg     420
gaaggagatc cctatccccct tctatctctc cgtctacttc tttgacgtca tgaaccccag   480
cgagatcctg aagggcgaga agccgcaggt gcgggagcgc gggccctacg tgtacaggga   540
gttcaggcac aaaagcaaca tcaccttcaa caacaacgac accgtgtcct tcctcgagta    600
ccgcaccttc cagttccagc cctccaagtc ccacggctcg gagagcgact acatcgtcat    660
gcccaacatc ctggtcttgg gtgcggcggt gatgatggag aataagccca tgaccctgaa    720
gctcatcatg accttggcat tcaccaccct cggcgaacgt gccttcatga accgcactgt    780
gggtgagatc atgtggggct acaaggaccc ccttgtgaat ctcatcaaca gtactttcc     840 aggcatgttc cccttcaagg acaagttcgg attattgct gagctcaaca actccgactc     900
tgggctcttc acggtgttca cggggtcca gaacatcagc aggatccacc tcgtggacaa    960
gtggaacggg ctgagcaagg ttgacttctg gcattccgat cagtgcaaca tgatcaatgg   1020
```

```
aacttctggg caaatgtggc cgccttcat gactcctgag tcctcgctgg agttctacag    1080
cccggaggcc tgccgatcca tgaagctaat gtacaaggag tcaggggtgt ttgaaggcat    1140
ccccacctat cgcttcgtgg ctcccaaaac cctgtttgcc aacgggtcca tctacccacc    1200
caacgaaggc ttctgcccgt gcctggagtc tggaattcag aacgtcagca cctgcaggtt    1260
cagtgccccc ttgtttctct cccatcctca cttcctcaac gctgaccgg ttctggcaga     1320 agcggtgact ggcctgcacc ctaaccagga ggcacactcc ttgttcctgg acatccaccc    1380
ggtcacggga atccccatga actgctctgt gaaactgcag ctgagcctct acatgaaatc    1440
tgtcgcaggc attggacaaa ctgggaagat tgagcctgtg gtcctgccgc tgctctggtt    1500
tgcagagagc ggggccatgg aggggagac tcttcacaca ttctacactc agctggtgtt     1560
gatgcccaag gtgatgcact atgcccagta cgtcctcctg gcgctgggct gcgtcctgct    1620
gctggtccct gtcatctgcc aaatccggag ccaagagaaa tgctatttat tttggagtag    1680
tagtaaaaag ggctcaaagg ataaggaggc cattcaggcc tattctgaat ccctgatgac    1740
atcagctccc aagggctctg tgctgcagga agcaaaactg tagggtcctg aggacaccgt    1800
gagccagcca ggcctggccg ctgggcctga ccggcccccc agcccctaca ccccgcttct    1860
cccggactct cccagcggac agccccccag ccccacagcc tgagcctccc agctgccatg    1920
tgcctgttgc acacctgcac acgccctg gcacacatac acatgcgt gcaggcttgt        1980 gcagacactc agggatggag ctgctgctga agggacttgt agggagaggc tcgtcaacaa    2040
gcactgttct ggaaccttct ctccacgtgg cccacaggcc tgaccacagg ggctgtgggt    2100
cctgcgtccc cttcctcggg tgagcctggc ctgtcccgtt cagccgttgg gcccaggctt    2160
cctcccctcc aaggtgaaac actgcagtcc cggtgtggtg gctccccatg caggacgggc    2220
caggctggga gtgccgcctt cctgtgccaa attcagtggg gactcagtgc ccaggccctg    2280
gccacgagct ttggccttgg tctacctgcc aggccaggca aagcgccttt acacaggcct    2340
cggaaaacaa tggagtgagc acaagatgcc ctgtgcagct gcccgagggt ctccgcccac    2400
cccggccgga ctttgatccc cccgaagtct tcacaggcac tgcatcgggt tgtctggcgc    2460
ccttttcctc cagcctaaac tgacatcatc ctatggactg agccggccac tctctggccg    2520
aagtggccgc aggctgtgcc cccgagctgc ccccacccc tcacagggtc cctcagatta    2580
taggtgccca ggctgaggtg aagaggcctg ggggccctgc cttccgggcg ctcctggacc    2640
ctggggcaaa cctgtgaccc ttttctactg aatagaaat gagttttatc atctttgaaa     2700
aataattcac tcttgaagta ataaacgttt aaaaaatgg gaaaaaaaa aaaaaaaaa       2759
```

<210> SEQ ID NO 7
<211> LENGTH: 2761
<212> TYPE: DNA
<213> ORGANISM: Mus musculus
<220> FEATURE:
<223> OTHER INFORMATION: DMPK mRNA

<400> SEQUENCE: 7

```
gaactggcca gagagaccca agggatagtc agggacgggc agacatgcag ctagggttct     60
ggggcctgga caggggcagc caggcccgt gacgggaaga ccccgagctc cggcccgggg      120
aggggccatg gtgttgcctg cccaacatgt cagccgaagt gcggctgagg cagctccagc    180
agctggtgct ggaccaggc ttcctgggac tggagcccct gctcgacctt ctcctgggcg     240
tccaccagga gctgggtgcc tctcacctag cccaggacaa gtatgtggcc gacttcttgc    300
```

```
agtgggtgga gcccattgca gcaaggctta aggaggtccg actgcagagg gatgattttg    360
agattttgaa ggtgatcggg cgtggggcgt tcagcgaggt agcggtggtg aagatgaaac    420
agacgggcca agtgtatgcc atgaagatta tgaataagtg ggacatgctg aagagaggcg    480
aggtgtcgtg cttccgggaa gaaagggatg tattagtgaa aggggaccgg cgctggatca    540
cacagctgca ctttgccttc caggatgaga actacctgta cctggtcatg gaatactacg    600
tgggcgggga cctgctaacg ctgctgagca gtttgggga gcggatcccc gccgagatgg    660
ctcgcttcta cctggccgag attgtcatgg ccatagactc cgtgcaccgg ctgggctacg    720
tgcacaggga catcaaacca gataacattc tgctggaccg atgtgggcac attcgcctgg    780
cagacttcgg ctcctgcctc aaactgcagc ctgatggaat ggtgaggtcg ctggtggctg    840
tgggcacccc ggactacctg tctcctgaga ttctgcaggc cgttggtgga gggcctgggg    900
caggcagcta cgggccagag tgtgactggt gggcactggg cgtgttcgcc tatgagatgt    960
tctatgggca gaccccccttc tacgcggact ccacagccga gacatatgcc aagattgtgc   1020
actacaggga acacttgtcg ctgccgctgg cagacacagt tgtccccgag gaagctcagg   1080
acctcattcg tgggctgctg tgtcctgctg agataaggct aggtcgaggt ggggcaggtg   1140
atttccagaa acatcctttc ttcttggcc ttgattggga gggtctccga cagtgtac     1200
ccccctttac accagacttc gagggtgcca cggacacatg caatttcgat gtggtggagg   1260
accggctcac tgccatggtg agcggggcg gggagacgct gtcagacatg caggaagaca   1320
tgccccttgg ggtgcgcctg cccttcgtgg gctactccta ctgctgcatg gccttcagag   1380
acaatcaggt cccggacccc accctatgg aactagaggc cctgcagttg cctgtgtcag   1440
acttgcaagg gcttgacttg cagcccccag tgtccccacc ggatcaagtg gctgaagagg   1500
ctgacctagt ggctgtccct gccctgtgg ctgaggcaga gaccacggta acgctgcagc   1560
agctccagga agccctggaa gaagaggttc tcacccggca gagcctgagc cgcgagctgg   1620
aggccatccg gaccgccaac cagaacttct ccagccaact acaggaggcc gaggtccgaa   1680
accgagacct ggaggcgcat gttcggcagc tacaggaacg gatggagatg ctgcaggccc   1740
caggagccgc agccatcacg gggtccccca gtccccgggc cacggatcca ccttcccatc   1800
tagatggccc cccggccgtg gctgtgggcc agtgcccgct ggtggggcca ggccccatgc   1860
accgccgtca cctgctgctc cctgccagga tccctaggcc tggcctatcc gaggcgcgtt   1920
gcctgctcct gttcgccgct gctctggctg ctgccgccac actgggctgc actgggttgg   1980
tggcctatac cggcggtctc accccagtct ggtgtttccc gggagccacc ttcgcccct    2040
gaaccctaag actccaagcc atctttcatt taggcctcct aggaaggtcg agcgaccagg   2100
gagcgaccca aagcgtctct gtgcccatcg cgcccccccc ccccccccac cgctccgctc   2160
cacacttctg tgagcctggg tccccaccca gctccgctcc tgtgatccag gctgccacc    2220
tggcggccgg ggagggagga acagggctcg tgcccagcac ccctggttcc tgcagagctg   2280
gtagccaccg ctgctgcagc agctgggcat tcgccgacct tgctttactc agccccgacg   2340
tggatgggca aactgctcag ctcatccgat ttcactttt cactctccca gccatcagtt   2400
acaagccata agcatgagcc cctatttcc agggacatcc cattcccata gtgatggatc   2460
agcaagacct ctgccagcac acacggagtc tttggcttcg gacagcctca ctcctggggg   2520
ttgctgcaac tccttccccg tgtacacgtc tgcactctaa caacggagcc acagctgcac   2580
tcccccctcc cccaaagcag tgtgggtatt tattgatctt gttatctgac tcactgacag   2640
actccgggac ccacgtttta gatgcattga gactcgacat tcctcggtat ttattgtctg   2700
```

```
tccccaccta cgacctccac tcccgaccct tgcgaataaa atacttctgg tctgccctaa      2760
a                                                                     2761

<210> SEQ ID NO 8
<211> LENGTH: 3243
<212> TYPE: DNA
<213> ORGANISM: Homo sapiens
<220> FEATURE:
<223> OTHER INFORMATION: DMPK mRNA

<400> SEQUENCE: 8
gccacaagcc tccaccccag ctggtccccc acccaggctg cccagtttaa cattcctagt        60
cataggacct tgacttctga gaggcctgat tgtcatctgt aaataagggg taggactaaa       120
gcactcctcc tggaggactg agagatgggc tggaccggag cacttgagtc tgggatatgt       180
gaccatgcta cctttgtctc cctgtcctgt tccttccccc agccccaaat ccagggtttt       240
ccaaagtgtg gttcaagaac cacctgcatc tgaatctaga ggtactggat acaaccccac       300
gtctgggccg ttacccagga cattctacat gagaacgtgg gggtggggcc ctggctgcac       360
ctgaactgtc acctggagtc agggtggaag gtggaagaac tggtcttcat ttccttctcc       420
ccttgttctt tagggtctgt ccttctgcag actccgttac cccaccctaa ccatcctgca       480 caccccttgga gccctctggg ccaatgccct gtcccgcaaa gggcttctca ggcatctcac       540
ctctatggga gggcattttt ggcccccaga accttacacg gtgtttatgt ggggaagccc       600
ctgggaagca gacagtccta gggtgaagct gagaggcaga gagaagggga gacagacaga       660
gggtggggct ttccccttg tctccagtgc cctttctggt gaccctcggt tcttttcccc       720 caccacccc ccagcggagc ccatcgtggt gaggcttaag gaggtccgac tgcagaggga       780
cgacttcgag attctgaagg tgatcggacg cggggcgttc agcgaggtag cggtagtgaa       840
gatgaagcag acgggccagg tgtatgccat gaagatcatg aacaagtggg acatgctgaa       900
gaggggcgag gtgtcgtgct tccgtgagga gagggacgtg ttggtgaatg ggaccggcg       960 gtggatcacg cagctgcact tcgccttcca ggatgagaac tacctgtacc tggtcatgga      1020
gtattacgtg ggcggggacc tgctgacact gctgagcaag tttggggagc ggattccggc      1080
cgagatggcg cgcttctacc tggcggagat tgtcatggcc atagactcgg tgcaccggct      1140
tggctacgtg cacagggaca tcaaacccga caacatcctg ctggaccgct gtggccacat      1200
ccgcctggcc gacttcggct cttgcctcaa gctgcgggca gatggaacgg tgcggtcgct      1260
ggtggctgtg ggcacccag actacctgtc ccccgagatc ctgcaggctg tgggcggtgg      1320
gcctgggaca ggcagctacg ggcccgagtg tgactggtgg gcgctgggtg tattcgccta      1380
tgaaatgttc tatgggcaga cgcccttcta cgcggattcc acggcggaga cctatggcaa      1440
gatcgtccac tacaaggagc acctctctct gccgctggtg gacgaagggg tccctgagga      1500
ggctcgagac ttcattcagc ggttgctgtg tcccccggag acacggctgg gccggggtgg      1560
```

-continued

```
agcaggcgac ttccggacac atcccttctt ctttggcctc gactgggatg gtctccggga    1620
cagcgtgccc cccttttacac cggatttcga aggtgccacc gacacatgca acttcgactt    1680
ggtggaggac gggctcactg ccatggtgag cggggcggg gagacactgt cggacattcg      1740
ggaaggtgcg ccgctagggg tccacctgcc ttttgtgggc tactcctact cctgcatggc     1800
cctcagggac agtgaggtcc caggcccccac acccatggaa ctggaggccg agcagctgct    1860
tgagccacac gtgcaagcgc ccagcctgga gccctcggtg tccccacagg atgaaacagc    1920
tgaagtggca gttccagcgg ctgtccctgc ggcagaggct gaggccgagg tgacgctgcg     1980
ggagctccag gaagccctgg aggaggaggt gctcacccgg cagagcctga gccgggagat     2040
ggaggccatc cgcacggaca accagaactt cgccagtcaa ctacgcgagg cagaggctcg     2100
gaaccgggac ctagaggcac acgtccggca gttgcaggag cggatggagt tgctgcaggc    2160
agagggagcc acagctgtca cggggtccc cagtccccgg gccacggatc caccttccca      2220
tctagatggc cccccggccg tggctgtggg ccagtgcccg ctggtggggc caggccccat    2280
gcaccgccgc cacctgctgc tccctgccag ggtccctagg cctggcctat cggaggcgct    2340
ttccctgctc ctgttcgccg ttgttctgtc tcgtgccgcc gccctgggct gcattgggtt     2400
ggtggcccac gccggccaac tcaccgcagt ctggcgccgc ccaggagccg cccgcgctcc    2460
ctgaacccta gaactgtctt cgactccggg gccccgttgg aagactgagt gcccggggca    2520
cggcacagaa gccgcgccca ccgcctgcca gttcacaacc gctccgagcg tgggtctccg    2580
cccagctcca gtcctgtgat ccgggcccgc ccctagcgg ccggggaggg aggggccggg     2640
tccgcggccg gcgaacgggg ctcgaagggt ccttgtagcc gggaatgctg ctgctgctgc    2700
tgctgctgct gctgctgctg ctgctgctgc tgctgctgct gctgctgggg ggatcacaga    2760
ccatttcttt ctttcggcca ggctgaggcc ctgacgtgga tgggcaaact gcaggcctgg    2820
gaaggcagca agccgggccg tccgtgttcc atcctccacg cacccccacc tatcgttggt    2880
tcgcaaagtg caaagctttc ttgtgcatga cgccctgctc tggggagcgt ctggcgcgat    2940
ctctgcctgc ttactcggga aatttgcttt tgccaaaccc gcttttttcgg ggatcccgcg    3000 ccccctcct cacttgcgct gctctcggag ccccagccgg ctccgcccgc ttcggcggtt     3060
tggatattta ttgacctcgt cctccgactc gctgacaggc tacaggaccc ccaacaaccc    3120
caatccacgt tttggatgca ctgagacccc gacattcctc ggtatttatt gtctgtcccc    3180
acctaggacc cccaccccg accctcgcga ataaaaggcc ctccatctgc ccaaagctct     3240
gga                                                                   3243
```

NUCLEIC ACID COMPLEX

CROSS-REFERENCE TO RELATED APPLICATIONS

This application is the U.S. National Stage of PCT/JP2019/010392, filed Mar. 13, 2019, which claims priority to JP 2018-047294, filed Mar. 14, 2018.

The instant application contains a Sequence Listing which has been submitted in ASCII format via EFS-WEB and is hereby incorporated by reference in its entirety. Said ASCII copy, created on Sep. 4, 2020, is named sequence.txt and is 36,918 bytes.

TECHNICAL FIELD

The present invention relates to a nucleic acid complex or a salt thereof that can provide an antisense effect in the nervous system, particularly the central nervous system, and to a composition or the like that contains the complex or a salt thereof.

BACKGROUND OF THE INVENTION

Recent interest has focused on oligonucleotides in the ongoing development of pharmaceuticals called nucleic acid pharmaceuticals, and, in particular, in view of the high selectivity and low toxicity of target genes, nucleic acid pharmaceuticals utilizing an antisense method is being actively developed. An antisense method comprises that the expression of a protein encoded by the target gene or the activity of the miRNA is selectively altered or inhibited, using the introduction of an oligonucleotide (an antisense oligonucleotide: herein, frequently referred to as an "ASO (AntiSense Oligonucleotide)") complementary to a target sense strand, a partial sequence of an mRNA or miRNA transcribed from a target gene, into cells.

Patent Literature 1 discloses a double-stranded nucleic acid molecule consisting of a first oligomer compound and a second oligomer compound containing a coupling group such as cholesterol and that can regulate the amount and activity of a target nucleic acid in the extrahepatic tissue or extrahepatic cell or in the hepatic tissue or hepatocyte, and an antisense compound consisting of the double-stranded nucleic acid molecule.

Now, a nucleic acid agent such as the ASO needs to be delivered to the central nervous system so that the antisense effect can be provided in the central nervous system including the brain. However, the brain has a mechanism called the blood brain barrier (Blood Brain Barrier: hereinafter, frequently referred to as the "BBB"), which selects and limits substances transferred to the brain via blood. This BBB mechanism protects the brain from harmful substances, but at the same time, forms a barrier against drug delivery to the brain. Because of this, there is a demand for a method of delivering a nucleic acid agent such as an ASO to the central nervous system including the brain.

CITATION LIST

Patent Literature

Patent Literature 1: WO2017/053999

SUMMARY OF THE INVENTION

Technical Problem

A purpose of the present invention is to provide a nucleic acid agent that is efficiently delivered to the nervous system, particularly the central nervous system, to which drug delivery is inhibited by the BBB mechanism, and that provides an antisense effect to a target transcription product at a delivery site, and a composition containing the nucleic acid agent.

Solution to Problem

To solve the problem mentioned above, the present inventors have investigated earnestly, and consequently have discovered that a nucleic acid complex wherein an ASO is annealed to a strand that is complementary to the ASO and bound to a phosphatidylethanolamine or an analogue thereof is efficiently delivered to the central nervous system and exhibits a high antisense effect there. Based on these discoveries, the present inventors have come to complete the present invention. Namely, the present invention encompasses the following.

(1) A nucleic acid complex or a salt thereof, comprising a first nucleic acid strand and a second nucleic acid strand (herein, these may frequently be referred to collectively as a "nucleic acid complex according to the present invention" for short), wherein the first nucleic acid strand comprises a base sequence capable of hybridizing with at least part of a target transcription product and has an antisense effect on the target transcription product; wherein the second nucleic acid strand comprises a base sequence complementary to the first nucleic acid strand and is bound to a phosphatidylethanolamine or an analog thereof; and wherein the first nucleic acid strand is annealed to the second nucleic acid strand.

(2) The nucleic acid complex or a salt thereof according to (1), wherein the phosphatidylethanolamine or an analog thereof is represented by the general formula I:

[Chem. 1]

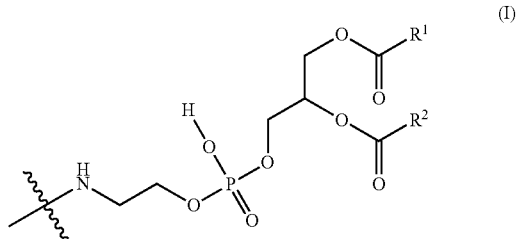

(wherein $R^1$ and $R^2$ independently represent a substituted or unsubstituted $C_5$-$C_{32}$ alkyl group, or a substituted or unsubstituted $C_5$-$C_{32}$ alkenyl group).

(3) The nucleic acid complex or a salt thereof according to (2), wherein $R^1$ and $R^2$ independently represent a $C_{15}$-$C_{19}$ alkyl group, or a $C_{17}$ alkenyl group.

(4) The nucleic acid complex or a salt thereof according to any one of (1) to (3), wherein the phosphatidylethanolamine or an analog thereof is represented by the general formulae XV to XXII:

[Chem. 2]
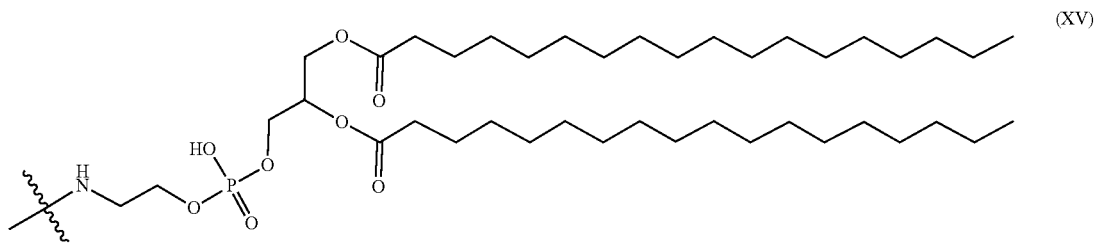
(XV)
[Chem. 3]
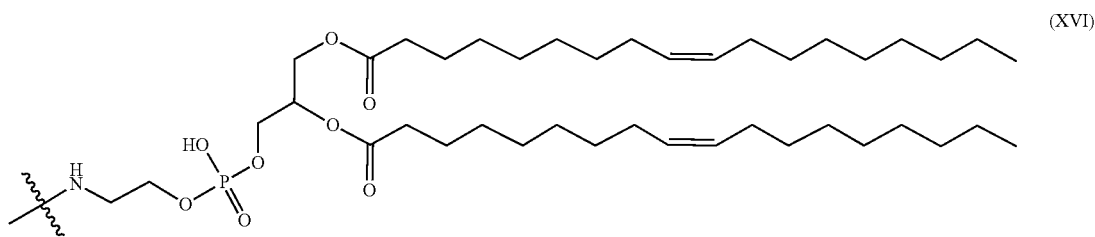
(XVI)
[Chem. 4]
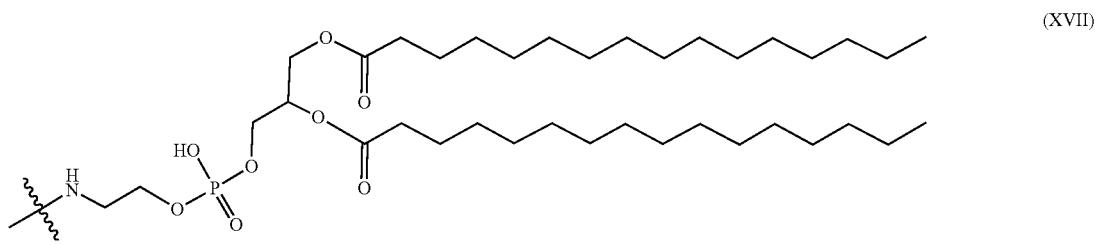
(XVII)
[Chem. 5]
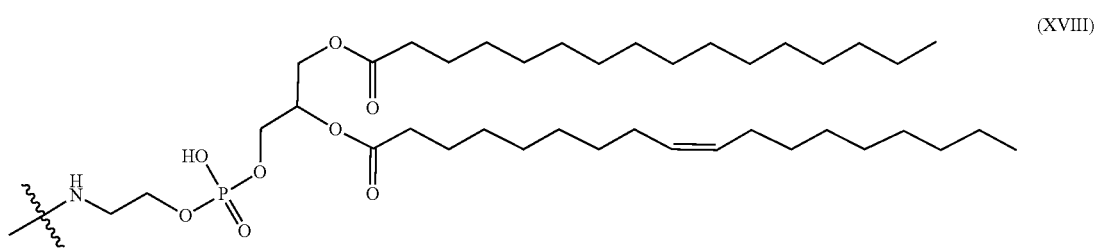
(XVIII)
[Chem. 6]
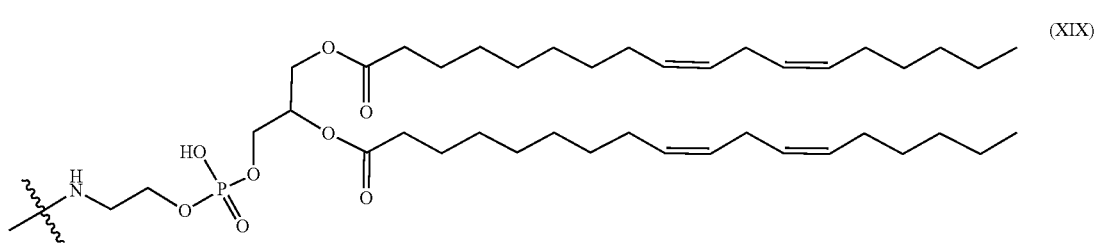
(XIX)
[Chem. 7]
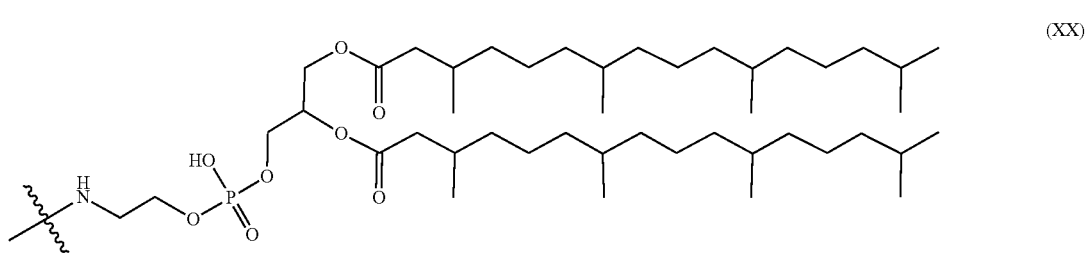
(XX)

[Chem. 8]

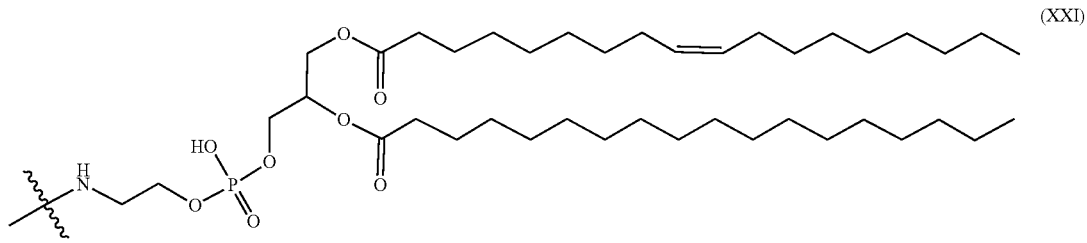

(XXI)

[Chem. 9]

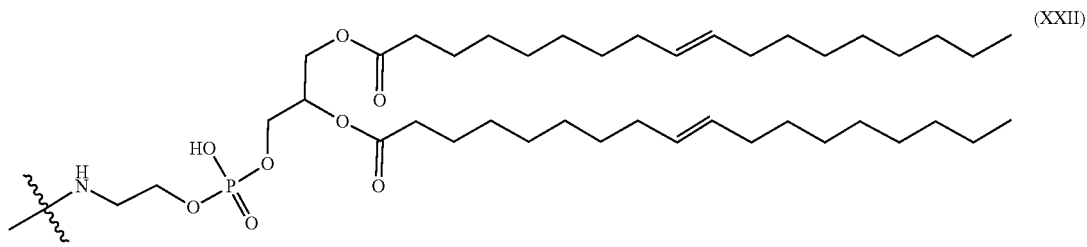

(XXII)

(5) The nucleic acid complex or a salt thereof according to any one of (1) to (4), wherein the second nucleic acid strand is bound to a phosphatidylethanolamine or an analog thereof via a linker represented by the general formula II:

[Chem. 10]

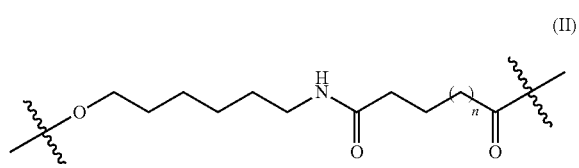

(II)

(wherein n is 0 or 1).

(6) The nucleic acid complex according to (5), wherein the 5' end of the second nucleic acid strand is bound to a phosphatidylethanolamine or an analog thereof via the linker.

(7) The nucleic acid complex or a salt thereof according to (5) or (6), wherein the phosphatidylethanolamine or an analog thereof bound via the linker is represented by the general formula III:

[Chem. 11]

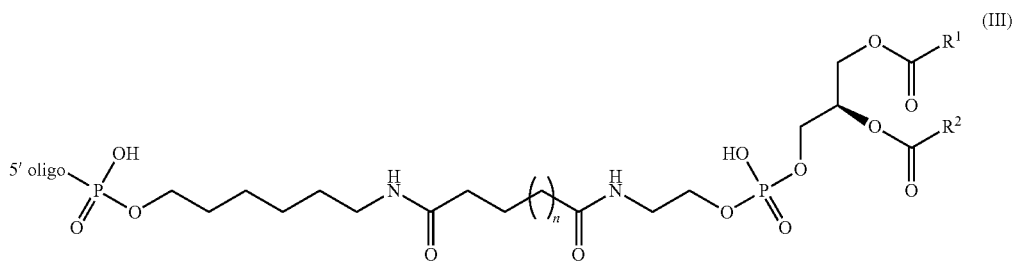

(III)

(wherein the 5' oligo represents the 5' end of an oligonucleotide; and wherein $R^1$ and $R^2$ have the same meaning as $R^1$ and $R^2$ described in the general formula I respectively, and n has the same meaning as n described in the general formula II).

(8) The nucleic acid complex or a salt thereof according to any one of (1) to (7), wherein the first nucleic acid strand comprises at least 4 consecutive deoxyribonucleosidedeoxyribonucleosides.

(9) The nucleic acid complex or a salt thereof according to any one of (1) to (8), wherein the first nucleic acid strand is a gapmer.

(10) The nucleic acid complex or a salt thereof according to (9), wherein the gapmer is an LNA/DNA gapmer.

(11) The nucleic acid complex or a salt thereof according to any one of (8) to (10), wherein the second nucleic acid strand comprises at least 4 consecutive ribonucleosides complementary to the at least 4 consecutive deoxyribonucleosides in the first nucleic acid strand.

(12) The nucleic acid complex or a salt thereof according to any one of (1) to (7), wherein the first nucleic acid strand is a mixmer.

(13) The nucleic acid complex or a salt thereof according to any one of (1) to (12), wherein the first nucleic acid strand has a length of 13 to 20 bases.

(14) The nucleic acid complex or a salt thereof according to any one of (1) to (13), wherein the second nucleic acid strand comprises no natural ribonucleoside.

(15) The nucleic acid complex or a salt thereof according to any one of (1) to (14), wherein the nucleic acid portion of the second nucleic acid strand consists of deoxyribonucleosides and/or sugar-modified nucleosides, which are linked by modified or unmodified internucleoside bonds.

(16) A composition for regulating the expression or editing of a target transcription product in the central nervous system, containing the nucleic acid complex or a salt thereof according to any one of (1) to (15).

(17) The composition according to (16) for the treatment of a central nervous system disease.

(18) A composition for delivering a central nervous system agent, containing the nucleic acid complex or a salt thereof according to any one of (1) to (15).

(19) The composition according to any one of (16) to (18), wherein the central nervous system is selected from the group consisting of cerebral cortex, basal ganglion, cerebral white matter, diencephalon, brainstem, cerebellum, and spinal cord.

(20) The composition according to any one of (16) to (18), wherein the central nervous system is selected from the group consisting of frontal lobe, temporal lobe, hippocampus, parahippocampal gyrus, parietal lobe, occipital lobe, striatum, globus pallidus, claustrum, thalamus, subthalamic nucleus, midbrain, substantia nigra, pons, medulla oblongata, cerebellar cortex, cerebellar nucleus, cervical spinal cord, thoracic spinal cord, and lumbar spinal cord.

(21) The composition according to any one of (16) to (20) for intravenous administration or subcutaneous administration.

(22) The composition according to any one of (16) to (21), wherein one dose of the composition contains 5 mg/kg or more of the nucleic acid complex or a salt thereof.

(23) The composition according to any one of (16) to (22), wherein the nucleic acid complex or a salt thereof permeates BBB.

The present application claims the priority to Japanese Patent Application No. 2018-047294, the entire disclosure of which is herein incorporated.

Effect of the Invention

The present invention can provide a nucleic acid agent that is efficiently delivered to the central nervous system and provides an antisense effect at a delivery site, and a composition containing the nucleic acid agent.

BRIEF DESCRIPTION OF THE DRAWINGS

FIG. 1a shows a nucleic acid complex in which a phosphatidylethanolamine is bound to the 5' end of the second nucleic acid strand, and FIG. 1b shows a nucleic acid complex in which a phosphatidylethanolamine is bound to the 3' end of the second nucleic acid strand. Phosphatidylethanolamines may be bound to both the 5' end and 3' end of the second nucleic acid strand, although it is not shown here.

DETAILED DESCRIPTION OF THE INVENTION

1. Nucleic Acid Complex

A first aspect of the present invention is a nucleic acid complex, more preferably a blood brain barrier-permeable nucleic acid complex. The nucleic acid complex comprises a first nucleic acid strand and a second nucleic acid strand. The second nucleic acid strand is a nucleotide strand comprising a base sequence complementary to the first nucleic acid strand. In the nucleic acid complex, the first nucleic acid strand is annealed to the second nucleic acid strand. In one embodiment, the second nucleic acid strand is bound to a phosphatidylethanolamine or an analog thereof.

Figure 1:
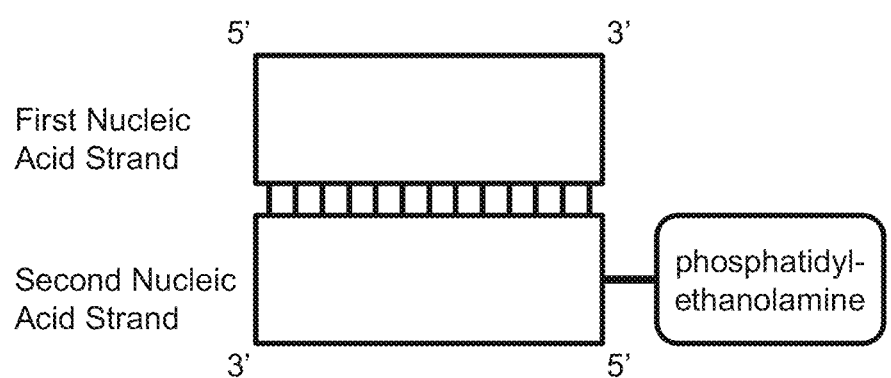
FIG. 1 is schematic diagrams showing a basic constitution of a nucleic acid complex according to the present invention. These diagrams show two patterns according to the binding position of a phosphatidylethanolamine in the second nucleic acid strand.
Figure 1:
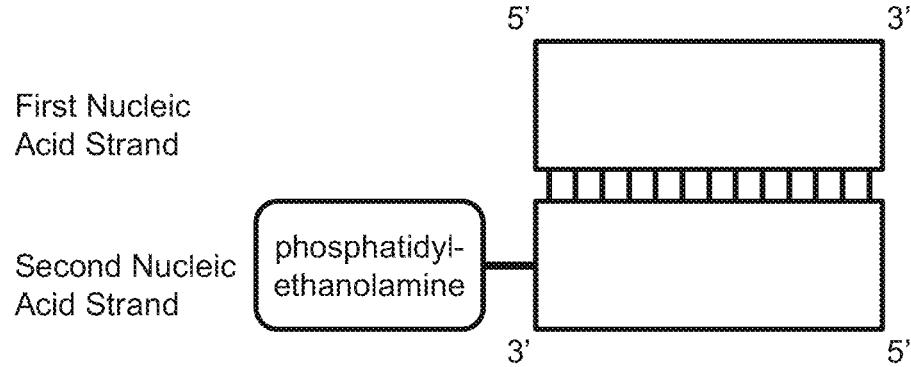

Typical schematic diagrams of the nucleic acid complex are shown in FIG. 1. FIG. 1a shows a nucleic acid complex, wherein a phosphatidylethanolamine is bound to the 5' end of the second nucleic acid strand. FIG. 1b shows a nucleic acid complex, wherein a phosphatidylethanolamine is bound to the 3' end of the second nucleic acid strand. Phosphatidylethanolamines or analogs thereof may be bound to both the 5' end and 3' end of the second nucleic acid strand, although it is not shown here. Furthermore, a phosphatidylethanolamine or an analog thereof may be bound to a nucleotide in the second nucleic acid strand.

In one embodiment, the first nucleic acid strand is a nucleotide strand comprising a base sequence capable of hybridizing with at least part of a target transcription product. In certain embodiment, the first nucleic acid strand is a nucleotide strand having an antisense effect on a transcription product of the target gene or on the target transcription product.

Definition of Terms

Herein, a "target transcription product" refers to any RNA that can be a target of a nucleic acid complex according to the present invention and is synthesized by a DNA-dependent RNA polymerase. In general, a transcription product of a target gene meets this definition. Specifically, an mRNA transcribed from a target gene (including a mature mRNA, mRNA precursor, mRNA without base modification, and the like) and a non-coding RNA (ncRNA) such as miRNA may be comprised.

Herein, an example of a "target gene" comprises, but is not particularly limited to, a gene derived from an organism to which a nucleic acid complex according to the present invention is to be introduced, such as a gene whose expression is increased in various diseases. Additionally, the target transcription product comprises an mRNA transcribed from genomic DNA encoding the target gene, and further includes an mRNA without base modification, mRNA precursor without being processed, and the like. A "target transcription product" can comprise not only an mRNA but also a non-coding RNA (ncRNA) such as an miRNA. Furthermore, in general, a "transcription product" may be any RNA synthesized by a DNA-dependent RNA polymerase. In one embodiment, a "target transcription product" may be, for example, a scavenger receptor B1 (hereinafter, frequently referred to as an "SR-B1 mRNA") or a metastasis associated lung adenocarcinoma transcript 1 (hereinafter, frequently referred to as a "Malat1") non-coding RNA. The base sequence of a mouse Malat1 non-coding RNA is shown in SEQ ID NO: 3, and the base sequence of a human Malat1 non-coding RNA is shown in SEQ ID NO: 4. Additionally, the base sequence of a mouse SR-B1 mRNA is shown in SEQ ID NO: 5, and the base sequence of a human SR-B1 mRNA is shown in SEQ ID NO: 6. Furthermore, the base sequence of a mouse DMPK mRNA is shown in SEQ ID NO: 7, and the base sequence of a human DMPK mRNA is shown in SEQ ID NO: 8. In each of SEQ ID NOs: 1 to 8, the base sequence of the mRNA is replaced by the base sequence of the DNA. Information on the base sequences of these genes and transcription products is available from, for example, a known database such as the NCBI (National Center for Biotechnology Information, the U.S.A.) database.

As used herein, an "antisense oligonucleotide (ASO)" or "antisense nucleic acid" refers to a single-stranded oligonucleotide which comprises a complementary base sequence capable of hybridizing with at least a part, for example, any target region of a target transcription product, and which can suppressively control the expression of the transcription product of a target gene or the level of the target transcription product by means of an antisense effect. In a nucleic acid complex according to the present invention, the first nucleic acid strand functions as an ASO, and the target region may comprise a 3' UTR, 5' UTR, exon, intron, coding region, translation initiation region, translation termination region, or any other nucleic acid region. The target region of a target transcription product can have a length of at least 8 bases, for example, a length of 10 to 35 bases, a length of 12 to 25 bases, a length of 13 to 20 bases, a length of 14 to 19 bases, or a length of 15 to 18 bases.

Figure 2:
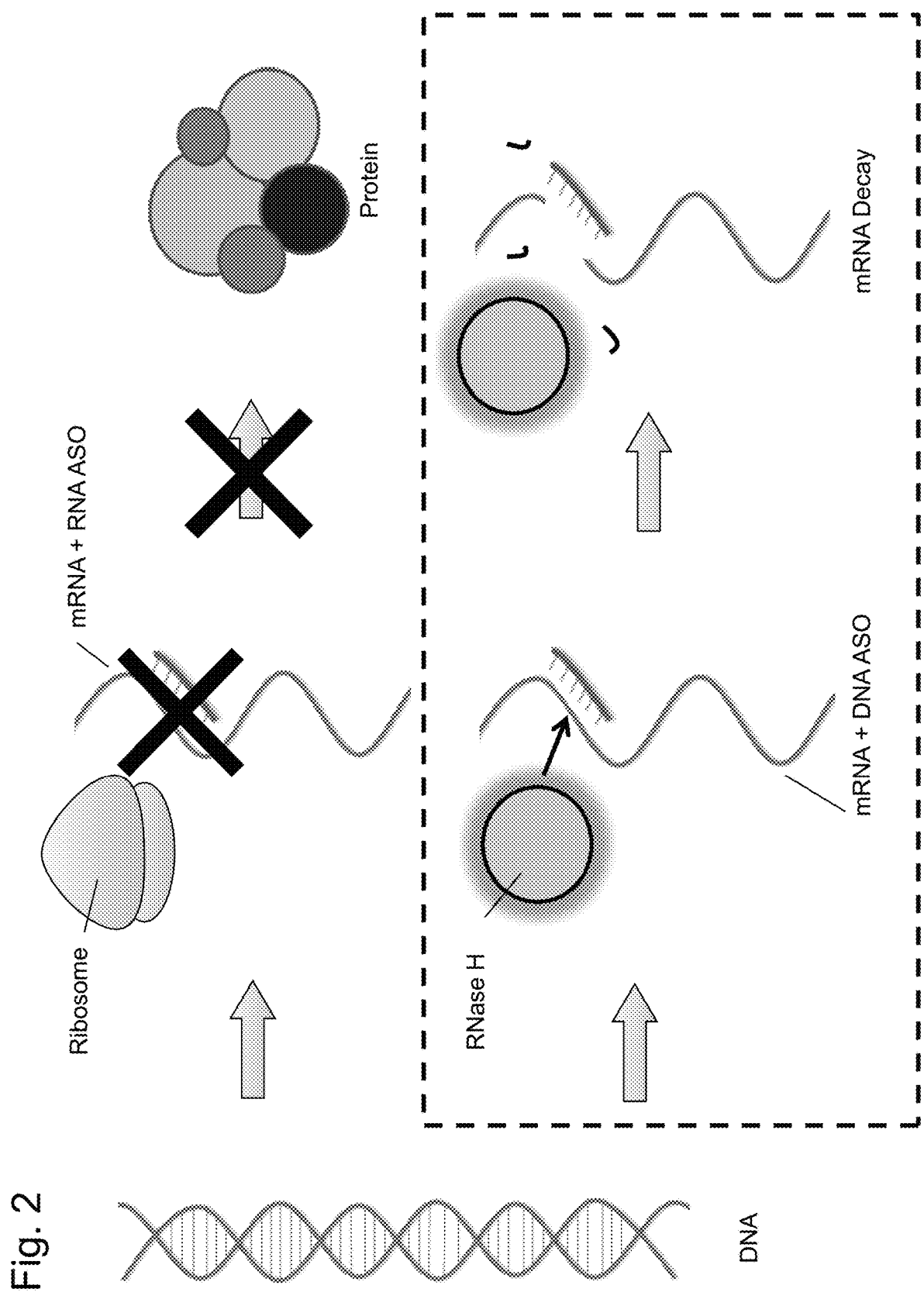
FIG. 2 is a diagram showing an example of a general mechanism of an antisense method. In the diagram, "X" represents a point of suppression or inhibition in the step from the expression to translation of a gene. The diagram in the dashed line is a schematic diagram showing that a heteroduplex portion is recognized by an RNase H, and the mRNA of a target gene is degraded.

An "antisense effect" refers to an effect that is provided to regulate expression or editing of a target transcription product by the hybridization of an ASO with the target transcription product (for example, an RNA sense strand). The phrase "regulate expression or editing of a target transcription product" refers to: suppression of or a decrease in the expression of a target gene or the expression amount of a target transcription product (hereinafter, the "expression amount of a target transcription product" is frequently referred to as the "level of a target transcription product"); translation inhibition; a splicing function alteration effect (for example, exon-skipping and the like); or degradation of a transcription product. For example, in translation inhibition, if an oligonucleotide (e.g., an RNA) is introduced as an ASO into a cell, the ASO is bound to an mRNA, which is a transcription product of a target gene, or the like, to form a partial double-strand, as shown in FIG. 2. This partial double-strand plays a role as a cover for inhibiting translation by ribosome, and accordingly, the expression of a protein encoded by the target gene is inhibited at translation level (the X marked outside the dashed line in FIG. 2). On the other hand, if an oligonucleotide, which contains DNA, introduced as an ASO into a cell, a partial DNA-RNA heteroduplex is formed. This heteroduplex structure is recognized by an RNase H, and, as a result, the mRNA of the target gene is degraded, and accordingly, the expression of a protein encoded by the target gene is inhibited at expression level (in the dashed line in FIG. 2). This is referred to as an "RNase-H dependent pathway". Furthermore, in certain example, an antisense effect can be provided by targeting the introns of an mRNA precursor. The antisense effect may also be provided by targeting an miRNA, in this case, the function of the miRNA is inhibited, and the expression of a gene the expression of which is usually regulated by the miRNA can increase. In one embodiment, regulation of expression of a target transcription product may be a decrease in the amount of a target transcription product.

As used herein, the term "nucleic acid" or "nucleic acid molecule" refers to a nucleoside or nucleotide as is in a monomer, an oligonucleotide as is in an oligomer, or a polynucleotide as is in a polymer.

A "nucleoside" generally refers to a molecule consisting of a combination of a base and a sugar. The sugar portion of a nucleoside is, without limitation, usually constituted with a pentofuranosyl sugar, specific example thereof comprising ribose and deoxyribose. The base portion of a nucleoside (a nucleic acid base) is usually a heterocyclic base portion. It comprises, but is not limited to, adenine, cytosine, guanine, thymine, or uracil, and modified nucleic acid bases (modified bases) other than them.

A "nucleotide" refers to a molecule in which a phosphate group is covalently bonded to the sugar portion of the nucleoside. In a nucleotide comprising a pentofuranosyl sugar, a phosphate group is usually linked to the hydroxyl group at the 2' position, 3' position, or 5' position of the sugar.

An "oligonucleotide" refers to a linear oligomer formed by a few to tens of nucleotides linked, wherein the hydroxyl group of the sugar portion and the phosphate group are covalently bonded between neighboring nucleotides. Further, a "polynucleotide" refers to a linear polymer formed by nucleotides more than an oligonucleotide, for example, tens or more, preferably hundreds or more of nucleotides linked, with said covalent bond. In general, a phosphate group is considered to form an internucleoside bond at the inside of the oligonucleotide or polynucleotide structure.

As used herein, the term "nucleic acid strand", or more simply "strand", refers to an oligonucleotide or polynucleotide. A nucleic acid strand, as a full-length strand or partial strand, can be produced, for example, by a chemical synthesis method using an automated synthesis device, or by an enzymic step using a polymerase, ligase, or restriction reaction. A nucleic acid strand can comprise a natural nucleotide and/or an unnatural nucleotide.

As used herein, a "natural nucleoside" refers to a nucleoside that is present in nature. For example, it comprises a ribonucleoside consisting of a ribose and the base such as adenine, cytosine, guanine, or uracil, and a deoxyribonucleoside consisting of a deoxyribose and the base such as adenine, cytosine, guanine, or thymine. In some cases, a ribonucleoside found in an RNA and a deoxyribonucleoside found in a DNA are referred to as a "DNA nucleoside" and an "RNA nucleoside" respectively. Similarly, a "natural nucleotide" refers to a nucleotide that is present in nature and that is a molecule in which a phosphate group is covalently bonded to the sugar portion of said natural nucleotide. For example, it comprises a ribonucleotide, known as a constituent unit of an RNA, in which a phosphate group is bound to a ribonucleoside, and a deoxyribonucleotide, known as a constituent unit of a DNA, in which a phosphate group is bound to a deoxyribonucleoside.

As used herein, an "unnatural nucleoside" refers to any nucleoside other than a natural nucleoside. For example, it comprises modified nucleosides and nucleoside mimics. As used herein, a "modified nucleoside" refers to a nucleoside having a modified sugar portion and/or a modified nucleic acid base. A nucleic acid strand comprising an unnatural oligonucleotide is often more preferable than a natural type because of the desirable characteristics, for example, enhancement of cell uptake, enhancement of affinity to a nucleic acid target, increase in stability in the presence of nuclease, or increase in inhibitory activity.

As used herein, a "mimic" refers to a functional group that substitutes a sugar, nucleic acid base, and/or internucleoside bond. In general, a mimic is used instead of a sugar or combination of a sugar and an internucleoside bond, and a nucleic acid base is maintained for hybridization with a selected target. A "nucleoside mimic" comprises a structure used at 1 or more positions in an oligomer compound to substitute a sugar, to substitute a sugar and a base, or to substitute, for example, a bond between monomer subunits constituting the oligomer compound. An "oligomer compound" refers to a polymer of some linked monomer subunits at least capable of hybridizing with a region of a nucleic acid molecule. A nucleoside mimic comprises, for example, a morpholino, cyclohexenyl, cyclohexyl, tetrahydropyranyl, and a bicyclic or tricyclic sugar mimic, such as a nucleoside mimic having a non-furanose sugar unit.

Figure 3:
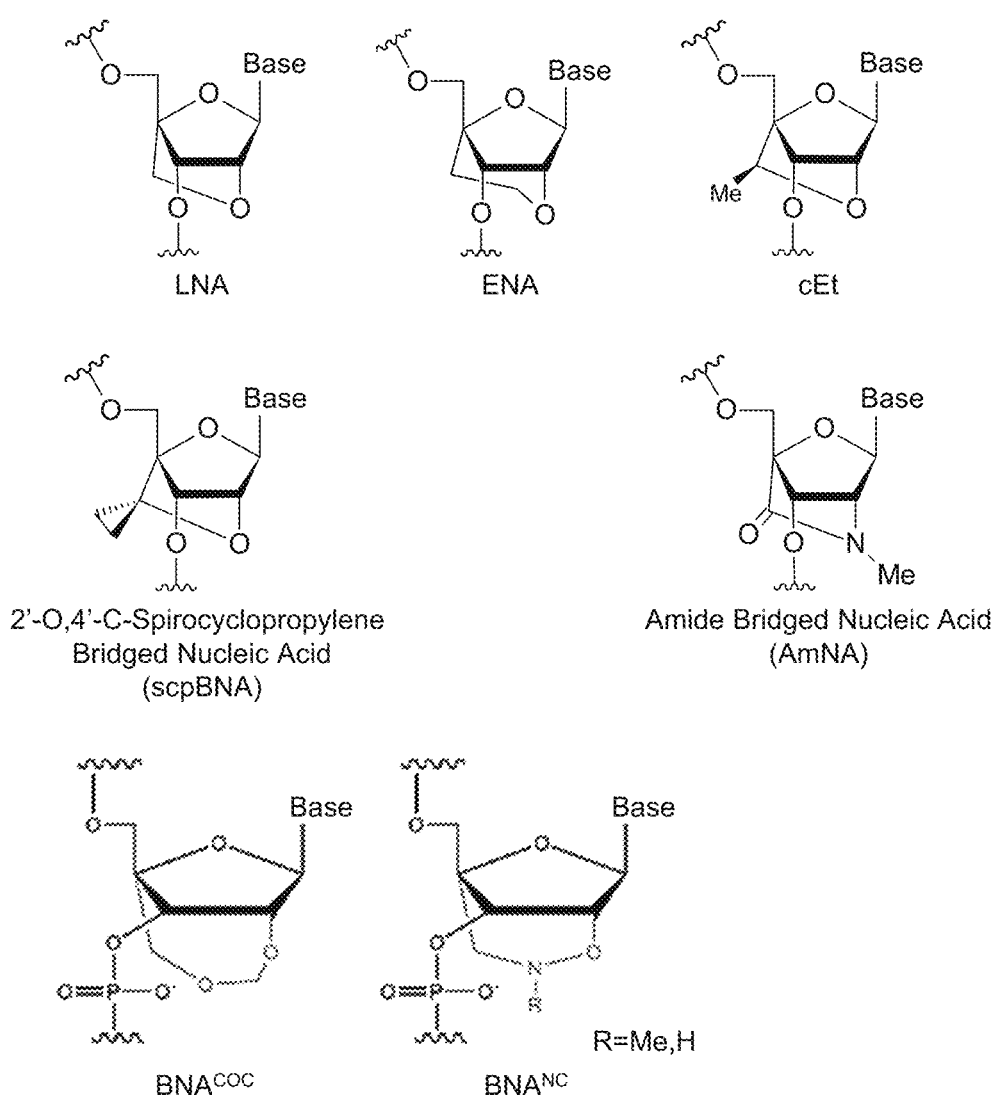
FIG. 3 is a diagram showing the structures of various bridged nucleic acids.

As used herein, a "bicyclic nucleoside" refers to a modified nucleoside comprising a bicyclic sugar portion. In general, a nucleic acid comprising a bicyclic sugar portion is referred to as a bridged nucleic acid (BNA). Herein, a nucleoside comprising a bicyclic sugar portion may be referred to as a "bridged nucleoside". FIG. 3 shows some examples of the bridged nucleic acid.

A bicyclic sugar may be a sugar in which the 2' position carbon atom and 4' position carbon atom are bridged by 2 or more atoms. Example of bicyclic sugar is known to a person skilled in the art. One subgroup of a nucleic acid comprising a bicyclic sugar (BNA) can be described as having a 2' position carbon atom and 4' position carbon atom that are bridged by 4'-$(CH_2)_p$—O-2', 4'-$(CH_2)_p$—$CH_2$-2', 4'-$(CH_2)_p$—S-2', 4'-$(CH_2)_p$—O $CH_2$O-2', or 4'-$(CH_2)_n$—N($R_3$)—O—$(CH_2)_m$-2' [wherein p, m, and n represent an integer of 1 to 4, an integer of 0 to 2, and an integer of 1 to 3 respectively; $R_3$ represents a hydrogen atom, alkyl group, alkenyl group, cycloalkyl group, aryl group, aralkyl group, acyl group, sulfonyl group, or unit substituent (fluorescence- or chemiluminescence-labeled molecule, functional group having nucleic acid cleaving activity, intracellular or intranuclear localization signal peptide, or the like)]. Furthermore, in the $OR_2$ substituent at the 3' position carbon atom and the $OR_1$ substituent at the 5' position carbon atom in BNA according to certain embodiment, $R_1$ and $R_2$ are typically hydrogen atoms and may be the same as or different from each other, and further, they may be a protecting group for a hydroxyl group for nucleic acid synthesis, alkyl group, alkenyl group, cycloalkyl group, aryl group, aralkyl group, acyl group, sulfonyl group, silyl group, phosphate group, phosphate group protected by a protecting group for nucleic acid synthesis, or P($R_4$)$R_5$ [wherein $R_4$ and $R_5$ may be the same as or different from each other, and each represents a hydroxyl group, hydroxyl group protected by a protecting group for nucleic acid synthesis, mercapto group, mercapto group protected by a protecting group for nucleic acid synthesis, amino group, alkoxy group having 1 to 5 carbon atoms, alkylthio group having 1 to 5 carbon atoms, cyanoalkoxy group having 1 to 6 carbon atoms, or amino group substituted with alkyl group having 1 to 5 carbon atoms]. Non-limiting example of such BNA comprises methyleneoxy (4'-$CH_2$—O-2') BNA (LNA (Locked Nucleic Acid (registered trademark), also known as 2',4'-BNA), such as α-L-methyleneoxy (4'-$CH_2$—O-2') BNA or β-D-methyleneoxy (4'-$CH_2$—O-2') BNA; ethyleneoxy (4'-$(CH_2)_2$—O-2') BNA (also known as ENA); β-D-thio(4'-$CH_2$—S-2') BNA; aminooxy(4'-$CH_2$—O—N($R_3$)-2') BNA; oxyamino (4'-$CH_2$—N($R_3$)—O-2') BNA (also known as 2',4'-$BNA^{NC}$); 2',4'-$BNA^{coc}$; 3'-amino-2',4'-BNA; 5'-methyl BNA; (4'-CH($CH_3$)—O-2') BNA (also known as cEt BNA); (4'-CH($CH_2OCH_3$)—O-2') BNA (also known as cMOE BNA); amide BNA (4'-C(O)—N(R)-2') BNA (R=H, Me) (also known as AmNA); 2'-O,4'-C-spirocyclopropylene bridged nucleic acid (also known as scpBNA); and others BNAs known to a person skilled in the art. Herein, a bicyclic nucleoside having a methyleneoxy (4'-$CH_2$—O-2') bridge may be referred to as an "LNA nucleoside".

As used herein, an "unnatural nucleotide" refers to any nucleotide other than a natural nucleotide and comprises a modified nucleotide and a nucleotide mimic. As used herein, a "modified nucleotide" refers to a nucleotide having any 1 or more of a modified sugar portion, a modified internucleoside bond, and a modified nucleic acid base.

Figure 4:
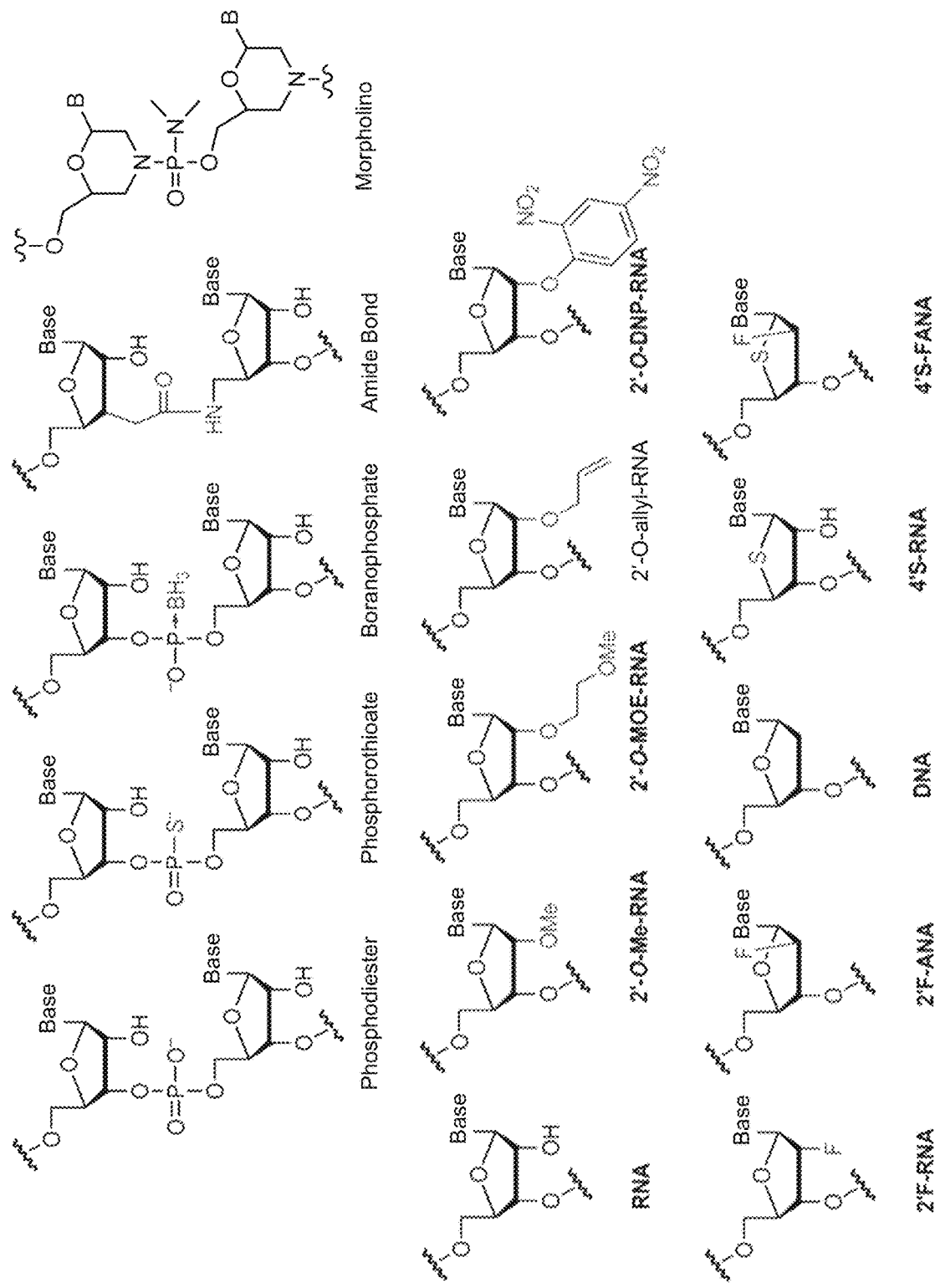
FIG. 4 is a diagram showing the structures of various natural nucleotides or unnatural nucleotides.

A "nucleotide mimic" comprises a structure used to substitute a nucleoside and a bond at 1 or more positions in an oligomer compound. A nucleotide mimic comprises, for example, a peptide nucleic acid or a morpholino nucleic acid (a morpholino bound by —N(H)—C(=O)—O— or other non-phosphodiester bond). A peptide nucleic acid (Peptide Nucleic Acid: PNA) is a nucleotide mimic having a main-chain to which N-(2-aminoethyl)glycine instead of a sugar is bound by an amide bond. An example of the structure of a morpholino nucleic acid is shown in FIG. 4. Herein, a nucleic acid strand comprising an unnatural oligonucleotide often has desirable characteristics, for example, enhancement of cell uptake, enhancement of affinity to a nucleic acid target, increase in stability in the presence of nuclease, or increase in inhibitory activity, or the like. Accordingly, it is more preferable than a natural nucleotide.

As used herein, a "modified internucleoside bond" refers to an internucleoside bond having a substitution or any change from a naturally-occurring internucleoside bond (in other words, a phosphodiester bond). A modified internucleoside linkage comprises a phosphorus-comprising internucleoside bond comprising a phosphorus atom and a non-phosphorus-comprising internucleoside bond comprising no phosphorus atom. Typical phosphorus-comprising internucleoside bond comprises, but is not limited to, a phosphodiester bond, phosphorothioate bond, phosphorodithioate bond, phosphotriester bond, alkylphosphonate bond, alkylthiophosphonate bond, boranophosphate bond, phosphoramidate bond, and the like. A phosphorothioate bond is an internucleoside bond formed by substituting the non-bridged oxygen atom of a phosphodiester bond with a sulfur atom. Methods of preparing phosphorus-comprising and non-phosphorus-comprising bonds are well known. The modified internucleoside bond preferably is a bond with a higher nuclease resistance than naturally-occurring internucleoside bonds.

As used herein, a "modified nucleic acid base" or "modified base" refers to any nucleic acid base other than adenine, cytosine, guanine, thymine, or uracil. Example of modified nucleic acid base comprises, but is not limited to, 5-methylcytosine, 5-fluorocytosine, 5-bromocytosine, 5-iodocytosine, N4-methylcytosine, N6-methyladenine, 8-bromoadenine, N2-methylguanine, and 8-bromoguanine A preferable modified nucleic acid base is 5-methylcytosine. An "unmodified nucleic acid base" or "unmodified base" has the same meaning as a natural nucleic acid base, and refers to adenine (A) and guanine (G) which are purine bases and to thymine (T), cytosine (C), and uracil (U) which are pyrimidine bases.

As used herein, a "modified sugar" refers to a sugar having a substitution and/or any change from a natural sugar portion (in other words, a sugar portion found in DNA (2'-H)

or RNA (2'-OH)). Herein, a nucleic acid strand optionally comprises 1 or more modified nucleosides comprising a modified sugar. A sugar-modified nucleoside can confer enhancement of nuclease stability, an increase in binding affinity, or any other useful biological characteristics on a nucleic acid strand. A nucleoside may comprise a chemically-modified ribofuranose ring portion. Example of a chemically-modified ribofuranose ring comprises, but is not limited to, those resulting from: addition of a substituent (including 5' and 2' substituents); formation of a bicyclic nucleic acid (bridged nucleic acid, or BNA) by bridge-formation of non-geminal ring atoms; substitution of an oxygen atom with S, N(R), or C(R1)(R2) (R, R1, and R2 independently represent H, $C_1$-$C_{12}$ alkyl, or a protecting group) in a ribosyl ring; and combinations thereof. Herein, example of a nucleoside having a modified sugar portion comprises, but is not limited to, a nucleoside comprising a 5'-vinyl, 5'-methyl (R or S), 4'-S, 2'-F (2'-fluoro group), 2'-OCH$_3$ (2'-OMe group or 2'-O-methyl group), and 2'-O(CH$_2$)$_2$OCH$_3$ substituent. The substituent at the 2' position can be selected from allyl, amino, azido, thio, —O-allyl, —O—$C_1$-$C_{10}$ alkyl, —OCF$_3$, —O(CH$_2$)$_2$SCH$_3$, —O(CH$_2$)$_2$—O—N(Rm)(Rn), and —O—CH$_2$—C(=O)—N(Rm)(Rn), and Rm and Rn independently represent H or a substituted or unsubstituted $C_1$-$C_{10}$ alkyl. As used herein, a "2'-modified sugar" refers to a furanosyl sugar modified at the 2' position.

Methods of preparing a modified sugar are well known to a person skilled in the art. In a nucleotide having a modified sugar portion, a nucleic acid base portion (natural one, modified one, or a combination thereof) may be maintained for hybridization with a suitable nucleic acid target.

In general, modification can be performed so that nucleotides in the same strand can independently be modified differently. Additionally, to provide resistance to enzymic cleavage, the same nucleotide can have a modified internucleoside bond (for example, a phosphorothioate bond) and further have a modified sugar (for example, a 2'-O-methyl modified sugar or a bicyclic sugar). The same nucleotide can also have a modified nucleic acid base (for example, 5-methylcytosine) and further have a modified sugar (for example, a 2'-O-methyl modified sugar or a bicyclic sugar).

The number, kind, and position of unnatural nucleotides in a nucleic acid strand can have an impact on an antisense effect, and the like provided by the nucleic acid complex according to the present invention. The selection of a modification can vary depending on the sequence of a target gene and the like, but a person skilled in the art can determine a suitable embodiment by reference to the explanation in literatures related to an antisense method (for example, WO2007/143315, WO2008/043753, and WO 2008/049085). Furthermore, if an antisense effect of a nucleic acid complex according to the present invention obtained after modification is measured, and if a measured value obtained as such is not significantly lower than a measured value of the nucleic acid complex according to the present invention before modification (for example, if a measured value obtained after modification is 70% or more, 80% or more, or 90% or more of a measured value of the nucleic acid complex according to the present invention before modification), a related modification can be evaluated.

As used herein, the term "complementary" refers to a relationship in which a nucleic acid base is capable of forming what is called a Watson-Crick base pair (natural type base pair) or a non-Watson-Crick base pair (Hoogsteen base pair) via hydrogen bond. In the present invention, the first nucleic acid strand does not need to be completely complementary to at least part of a target transcription product (for example, a transcription product of a target gene), and it is acceptable that the base sequence has a complementarity of at least 70%, preferably at least 80%, more preferably at least 90% (for example, 95%, 96%, 97%, 98%, or 99% or more). Similarly, a complementary region in the second nucleic acid strand does not need to be completely complementary to at least a part of the first nucleic acid strand, and it is acceptable that the base sequence has a complementarity of at least 70%, preferably at least 80%, more preferably at least 90% (for example, 95%, 96%, 97%, 98%, or 99% or more).

As used herein, an "alkyl" refers to a linear or branched acyclic saturated aliphatic hydrocarbon. For example, a linear or branched alkyl group having 1 to 32 carbons comprises methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, octyl, decyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecane-2-yl, nonadecyl, 2,6,10,14-tetramethylpentadecyl, icosyl, 3,7,11,15-tetramethylhexadecyl, henicosyl, docosyl, tricosyl, tetracosyl, and the like.

As used herein, an "alkenyl" refers to a linear or branched alkenyl comprising at least 1 double bond. Alkenyl comprises both a cis isomer and trans isomer. For example, a $C_2$-$C_{32}$ linear or branched alkenyl group having 1 to 32 carbons comprises ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 8-heptadecenyl, (E)-8-heptadecenyl, (Z)-8-heptadecenyl, heptadec-8,11-dienyl, (8Z,11Z)-heptadec-8,11-dienyl, (8E, 11E)-heptadec-8,11-dienyl, (8Z,11E)-heptadec-8,11-dienyl, (8E, 11Z)-heptadec-8,11-dienyl, tetradeca-9-enyl, (Z)-tetradeca-9-enyl, (Z)-hexadeca-9-enyl, octadeca-6-enyl, (Z)-octadeca-6-enyl, octadeca-9-enyl, (Z)-octadeca-9-enyl, (E)-octadeca-9-enyl, octadeca-11-enyl, (Z)-octadeca-11-enyl, octadeca-9,12-dienyl, (9Z,12Z)-octadeca-9,12-dienyl, octadeca-9,12,15-trienyl, (9Z,12Z,15Z)-octadeca-9,12,15-trienyl, icos-11-enyl, (Z)-icos-11-enyl, icos-11,14-dienyl, (11Z,14Z)-icos-11,14-dienyl, 3,7,11-trimethyldodeca-2,6,10-trienyl, 3,7,11,15-tetramethylhexadeca-2-enyl, docosa-13-enyl, (Z)-docosa-13-enyl, and the like.

As used herein, the term "blood brain barrier (BBB)" refers to a mechanism that selects and limits substances transferred to the brain, and plays a role to protect the brain from harmful substances, as mentioned above.

As used herein, the term "central nervous system" is a tissue consisting of the brain and the spinal cord and that, together with the peripheral nervous system, constitutes the nervous system. The brain comprises the cerebrum (cerebral cortex, cerebral white matter, and basal ganglion), diencephalon (thalamus and subthalamic nucleus), cerebellum (cerebellar cortex, and cerebellar nucleus), and brainstem (midbrain, substantia nigra, pons, and medulla oblongata). Additionally, the spinal cord comprises the cervical spinal cord, thoracic spinal cord, lumbar spinal cord, sacral cord, and coccygeal cord. Herein, the central nervous system may be any region of these, and is preferably the cerebral cortex (frontal lobe, temporal lobe, parietal lobe, and occipital lobe), cerebellum, striatum, globus pallidus, claustrum, hippocampus, parahippocampal gyms, brainstem, cervical spinal cord, thoracic spinal cord, or lumbar spinal cord.

As used herein, a "salt thereof" refers to a salt of a nucleic acid complex according to the present invention wherein it is a physiologically and pharmaceutically acceptable salt of a nucleic acid complex according to the present invention, in other words, a salt that retains the desired biological activity of the nucleic acid complex and provides no undesired toxicological effect there. Such a salt comprises, for example, an alkali metal salt such as sodium salt, potassium salt, and lithium salt; alkaline earth metal salt such as calcium salt and magnesium salt; metal salt such as aluminium salt, iron salt, zinc salt, copper salt, nickel salt, and cobalt salt; inorganic salt such as ammonium salt; amine salt such as t-octylamine salt, dibenzylamine salt, morpholine salt, glucosamine salt, phenylglycinealkyl ester salt, ethylenediamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, tris(hydroxymethyl)aminomethane salt, diolamine salt, and meglumine salt; hydrohalic acid salt such as hydrofluoric acid salt, hydrochloric acid salt, hydrobromic acid salt, and hydroiodic acid salt; inorganic acid salt such as nitrate salt, perchlorate salt, sulfate salt, and phosphate salt; lower alkanesulfonate salt such as methanesulfonate salt, trifluoromethanesulfonate salt, and ethanesulfonate salt; arylsulfonate salt such as benzenesulfonate salt and p-toluenesulfonate salt; organic acid salt such as acetate salt, malate salt, fumarate salt, succinate salt, citrate salt, tartrate salt, oxalate salt, and maleate salt; and amino acid salt such as glycine salt, lysine salt, arginine salt, ornithine salt, glutamate salt, and aspartate salt.

In certain embodiment, a nucleic acid complex according to the present invention encompasses any pharmaceutically acceptable salt of the nucleic acid complex, esters of the nucleic acid complex, or salts of the ester. A preferable pharmaceutically acceptable salt comprises, but are not limited to, sodium salt, potassium salt, and meglumine salt.

Constitution of First Nucleic Acid Strand and Second Nucleic Acid Strand

The first nucleic acid strand comprises a base sequence capable of hybridizing with at least part of a target transcription product and is a single-stranded oligonucleotide strand that provides an antisense effect to the target transcription product.

The second nucleic acid strand is a single-stranded oligonucleotide strand comprising a base sequence complementary to the first nucleic acid strand. The second nucleic acid strand is bound to a phosphatidylethanolamine or an analog thereof. In the nucleic acid complex according to the present invention, the second nucleic acid strand is annealed to the first nucleic acid strand via the hydrogen bond between the complementary base pair.

The first nucleic acid strand and the second nucleic acid strand usually may have, without particular limitation, a length of at least 8 bases, a length of at least 9 bases, a length of at least 10 bases, a length of at least 11 bases, a length of at least 12 bases, a length of at least 13 bases, a length of at least 14 bases, or a length of at least 15 bases. In addition, the first nucleic acid strand and the second nucleic acid strand may have a length of 35 bases or less, a length of 30 bases or less, a length of 25 bases or less, a length of 24 bases or less, a length of 23 bases or less, a length of 22 bases or less, a length of 21 bases or less, a length of 20 bases or less, a length of 19 bases or less, a length of 18 bases or less, a length of 17 bases or less, or a length of 16 bases or less. The first nucleic acid strand and the second nucleic acid strand may have a length of about 100 bases, a length of 10 to 35 bases, a length of 12 to 25 bases, a length of 13 to 20 bases, a length of 14 to 19 base, or a length of 15 to 18 bases. The first nucleic acid strand and the second nucleic acid strand may have the same length or different lengths (for example, one of them has a length of 1 to 3 bases more or less than the other). The double-stranded structure formed by the first nucleic acid strand and the second nucleic acid strand may comprises a bulge. The selection of the length can be determined, for example, according to cost, a synthesis yield, and, among other factors, the balance between the intensity of an antisense effect and the specificity of a nucleic acid strand to a target.

A internucleoside bond in the first nucleic acid strand and the second nucleic acid strand may be a naturally-occurring internucleoside bond and/or modified internucleoside bond. Without limitation, at least 1, at least 2, or at least 3 internucleoside bonds from the end (the 5' end, the 3' end, or both ends) of the first nucleic acid strand and/or the second nucleic acid strand is/are preferably a modified internucleoside bonds. Here, for example, 2 internucleoside bonds from an end of a nucleic acid strand refer to an internucleoside bond most proximate to the end of the nucleic acid strand and an internucleoside bond located adjacent to it and at the other side of the end. A modified internucleoside bond in an end region of a nucleic acid strand is preferable, since it can suppress or inhibit undesired degradation of the nucleic acid strand. In one embodiment, all internucleoside bonds of the first nucleic acid strand and/or the second nucleic acid strand may be modified internucleoside bonds. The modified internucleoside bond may be a phosphorothioate bond.

At least 1 (for example, 3) internucleoside bonds from the 3' end of the second nucleic acid strand may be modified internucleoside bonds, such as a phosphorothioate bond having high RNase resistance. If a modified such as a phosphorothioate-modified, internucleoside bond is comprised at the 3' end of the second nucleic acid strand, it is preferable, since it enhances the gene suppression activity of the double-stranded nucleic acid complex.

At the 5' end and 3' end of the second nucleic acid strand, the internucleoside bonds between 2 to 6 bases from the end to which a phosphatidylethanolamine is not bound may be modified internucleoside bonds (for example, phosphorothioate bonds).

At least 1 (for example, 3) nucleosides from the 3' end of the second nucleic acid strand may be modified nucleosides such as a 2'F-RNA or 2'-OMe having high RNase resistance. If a modified nucleoside, such as a 2'F-RNA or 2'-OMe, comprised at the 3' end of the second nucleic acid strand, it is preferable, since it enhances the gene suppression activity of the double-stranded nucleic acid complex.

At the 5' end and 3' end of the second nucleic acid strand, 1 to 5 nucleosides from the end to which a phosphatidylethanolamine is not bound may be modified nucleosides such as a 2'F-RNA having high RNase resistance.

The nucleoside in the first nucleic acid strand and the second nucleic acid strand may be a natural nucleoside (deoxyribonucleoside, ribonucleoside, or both) and/or unnatural nucleoside.

Herein, the first nucleic acid strand can hybridize (or be annealed) with a target transcription product since the base sequence of the first nucleic acid is complementary to the base sequence of at least part of the target transcription product. The complementarity of a base sequence can be determined using a BLAST program or the like. A person skilled in the art can easily determine the conditions (temperature, salt concentration, and the like) that enable two strands to be hybridized, taking the degree of complementarity between strands into consideration. Furthermore, a person skilled in the art can easily design an antisense nucleic acid complementary to a target transcription product, for example, based on information of the base sequence of a target gene.

A hybridization condition may be, for example, various stringent conditions such as a low stringent condition and high stringent condition. The low stringent condition may be the condition with relatively low temperature and high salt concentration, for example 30° C., 2×SSC, and 0.1% SDS. The high stringent condition may be the condition with relatively high temperature and low salt concentration, for example 65° C., 0.1×SSC, and 0.1% SDS. The stringency of hybridization can be adjusted by changing the condition such as temperature and salt concentration. Here, 1×SSC contains 150 mM sodium chloride and 15 mM sodium citrate.

When hybridized with a target transcription product, the first nucleic acid strand can comprise at least 4, at least 5, at least 6, or at least 7 consecutive nucleosides that are recognized by RNase H. Usually, the region may comprise 4 to 20 bases, 5 to 16 bases, or 6 to 12 bases of consecutive nucleosides. As a nucleoside recognized by RNase H, for example, a natural type deoxyribonucleoside can be used. A suitable nucleoside including other bases, and modified deoxyribonucleoside are well known in the art. It is also known that a nucleoside having a hydroxy group at the 2' position, such as a ribonucleoside, is unsuitable as the said nucleoside. The suitability of a nucleoside regarding the use in the region comprising "at least 4 consecutive nucleosides" can easily be determined. In one embodiment, the first nucleic acid strand can comprise at least 4 consecutive deoxyribonucleosides.

In one embodiment, the full length of the first nucleic acid strand is not constituted only with natural ribonucleosides. It is preferable that half or less or none of the full length of the first nucleic acid strand is natural ribonucleosides.

In one embodiment, the second nucleic acid strand may comprise at least 4 consecutive ribonucleosides complementary to the above mentioned at least 4 consecutive nucleosides (for example, deoxyribonucleosides) in the first nucleic acid strand. This is because the second nucleic acid strand forms a partial DNA-RNA heteroduplex with the first nucleic acid strand so that it can be recognized and cleaved by RNase H. The at least 4 consecutive ribonucleosides in the second nucleic acid strand are preferably linked by naturally-occurring internucleoside bonds, i.e., phosphodiester bonds.

All nucleosides of the second nucleic acid strand may be constituted with ribonucleosides and/or modified nucleosides. All nucleosides of the second nucleic acid strand may be constituted with deoxyribonucleosides and/or modified nucleosides, or ribonucleoside may not be comprised.

The first nucleic acid strand and/or the second nucleic acid strand constituting a nucleic acid complex according to the present invention may be a gapmer(s). As used herein, a "gapmer" refers to a single-stranded nucleic acid consisting of the central region (DNA gap region), and the 5' wing region and 3' wing region located at both the 5' end and 3' end of the central region. The central region comprises at least 4 consecutive deoxyribonucleosides, and the 5' wing region and 3' wing region comprise an unnatural nucleoside. If the unnatural nucleosides constituting the 5' wing region and the 3' wing region comprise or consist of a bridged nucleoside, the gapmer is referred to as a "BNA/DNA gapmer" in particular. The number of bridged nucleosides comprised in the 5' wing region and the 3' wing region may be 2 or 3. The bridged nucleosides comprised in the 5' wing region and the 3' wing region may be present consecutively or inconsecutively in the 5' wing region and the 3' wing region. The bridged nucleoside can further comprises a modified nucleic acid base (for example, 5-methylcytosine). If the bridged nucleoside is an LNA nucleoside, the gapmer is referred to as an "LNA/DNA gapmer". If the unnatural nucleosides constituting the 5' wing region and the 3' wing region comprises or consist of a peptide nucleic acid, the gapmer is referred to as a "peptide nucleic acid gapmer" in particular. If the unnatural nucleosides constituting the 5' wing region and the 3' wing region comprises or consist of a peptide nucleic acid, the gapmer is referred to as a "morpholino nucleic acid gapmer" in particular. The 5' wing region and the 3' wing region may independently have a length of at least 2 bases, for example, a length of 2 to 10 bases, a length of 2 to 7 bases, or a length of 3 to 5 bases. The 5' wing region and 3' wing region may comprise at least 1 species of unnatural nucleoside, and may further comprise a natural nucleoside.

The first nucleic acid strand and/or the second nucleic acid strand constituting the gapmer may be constituted with bridged nucleosides having a length of 2 to 7 bases or a length of 3 to 5 bases; ribonucleosides or deoxyribonucleosides having a length of 4 to 15 bases or a length of 8 to 12 bases; and bridged nucleosides having a length of 2 to 7 bases or a length of 3 to 5 bases; in this order from the 5' end.

The first nucleic acid strand and/or the second nucleic acid strand constituting a nucleic acid complex according to the present invention may be a mixmer(s). As used herein, a "mixmer" refers to a nucleic acid strand that comprises alternative type of natural nucleosides and unnatural nucleosides with periodical or random segment length and that does not comprise 4 or more consecutive deoxyribonucleosides or ribonucleosides. Among mixmers, a mixmer in which the unnatural nucleoside is a bridged nucleoside and the natural nucleoside is a deoxyribonucleoside is referred to as a "BNA/DNA mixmer" in particular. Among mixmers, a mixmer in which the unnatural nucleoside is a peptide nucleic acid and the natural nucleoside is a deoxyribonucleoside is referred to as a "peptide nucleic acid/DNA mixmer" in particular. Among mixmers, a mixmer in which the unnatural nucleoside is a morpholino nucleic acid and the natural nucleoside is a deoxyribonucleoside is referred to as a "morpholino nucleic acid/DNA mixmer" in particular. A mixmer is not limited so as to comprise only two kinds of nucleosides. A mixmer can comprise any number of kinds of nucleosides regardless of being a natural or modified nucleoside or a nucleoside mimic. For example, it may have 1 or 2 consecutive deoxyribonucleosides separated by a bridged nucleoside (for example, an LNA nucleoside). The bridged nucleoside may further comprise a modified nucleic acid base (for example, 5-methylcytosine).

At least 1, at least 2, at least 3, or at least 4 nucleosides from the end (the 5' end, the 3' end, or both ends) of the second nucleic acid strand may be modified nucleosides. A modified nucleoside may comprise a modified sugar and/or a modified nucleic acid base. A modified sugar may be a 2'-modified sugar (for example, a sugar comprising a 2'-O-methyl group). The modified nucleic acid base can be 5-methylcytosine.

The second nucleic acid strand may be constituted with modified nucleosides (for example, modified nucleosides comprising a 2'-modified sugar) having a length of 2 to 7 bases or a length of 3 to 5 bases, ribonucleosides or deoxyribonucleosides (optionally linked by a modified internucleoside bond) having a length of 4 to 15 bases or a length of 8 to 12 bases, modified nucleosides (for example, modified nucleosides comprising a 2'-modified sugar) having a length of 2 to 7 bases or a length of 3 to 5 bases, in this order from the 5' end. In this case, the first nucleic acid strand may be a gapmer.

The first nucleic acid strand and the second nucleic acid strand may wholly or partially comprise a nucleoside mimic or a nucleotide mimic. The nucleotide mimic may be a peptide nucleic acid and/or a morpholino nucleic acid. The first nucleic acid strand may comprise at least 1 modified nucleoside. The modified nucleoside may comprise a 2'-modified sugar. This 2'-modified sugar may be a sugar comprising a 2'-O-methyl group.

The first nucleic acid strand and second nucleic acid strand may comprise any combination of the modified nucleosides and modified internucleoside bonds mentioned above.

The second nucleic acid strand is bound to a phosphatidylethanolamine (hereinafter, frequently referred to as a "PE") or an analog thereof.

A phosphatidylethanolamine (PE) is a neutral phospholipid having a structure in which an ethanolamine is ester-bonded to the phosphate group of a phosphatidic acid. A phosphatidic acid refers to a glycerophospholipid in which a variety of carboxyl group (fatty acid) is ester-bonded to a hydroxyl group at the 1-position and 2-position of a glycerol and a phosphoric acid is ester-bonded to the hydroxyl group at the 3-position. A PE is also called a cephalin, is an important constituent of a cell membrane of an organism, and functions for division, fusion, and maintenance of a cell membrane, and for stabilization of a membrane protein, and the like.

A group derived from a PE or an analog thereof to be bound to the second nucleic acid strand (hereinafter, it may be referred to as a "PE group" for short) is represented by the following general formula I.

[Chem. 12]

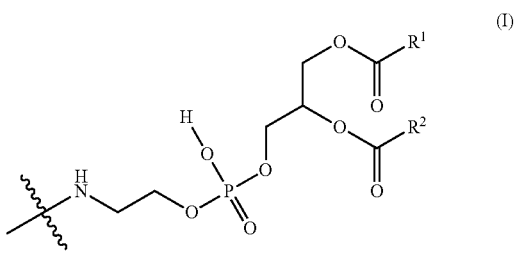

(I)

wherein $R^1$ and $R^2$ independently represent a substituted or unsubstituted $C_5$-$C_{32}$, preferably a $C_{15}$-$C_{19}$ alkyl group (e.g., pentadecyl, heptadecyl, or 2,6,10,14-tetramethylpentadecyl), more preferably a $C_{17}$ alkyl group (e.g., heptadecyl), or a substituted or unsubstituted $C_5$-$C_{32}$, preferably a $C_{17}$ alkenyl group (e.g., heptadecenyl (for example, 8-heptadecenyl (e.g., (E)-8-heptadecenyl or (Z)-8-heptadecenyl) or heptadec-8,11-dienyl (e.g., (8E,11E)-heptadec-8,11-dienyl)).

In one embodiment, a group derived from a PE or an analog thereof to be bound to the second nucleic acid strand is represented by the following general formulae XV to XXII:

[Chem. 13]

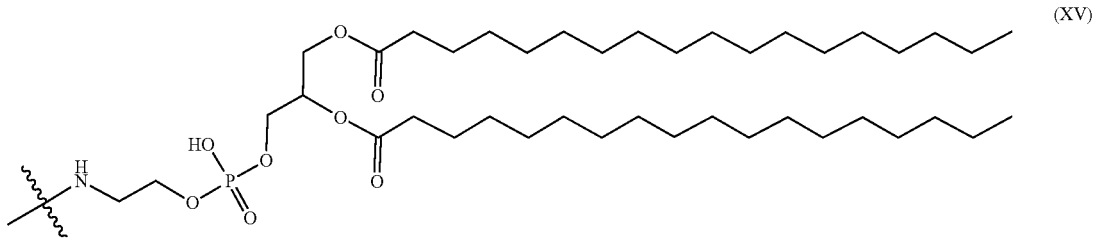

(XV)

[Chem. 14]

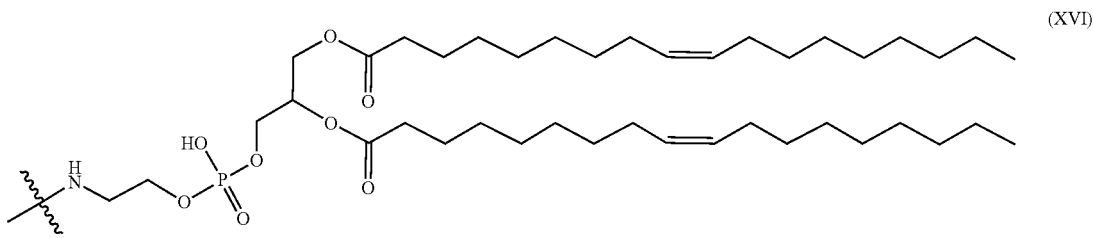

(XVI)

[Chem. 15]
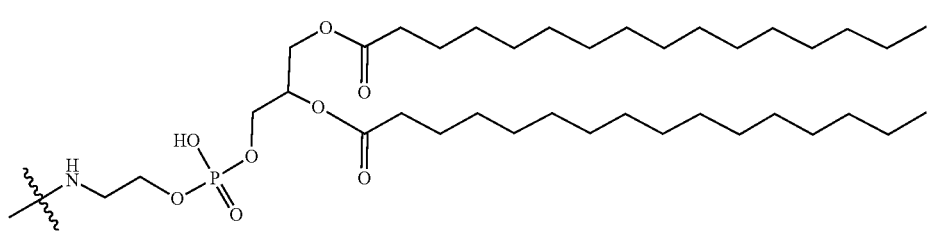
(XVII)
[Chem. 16]
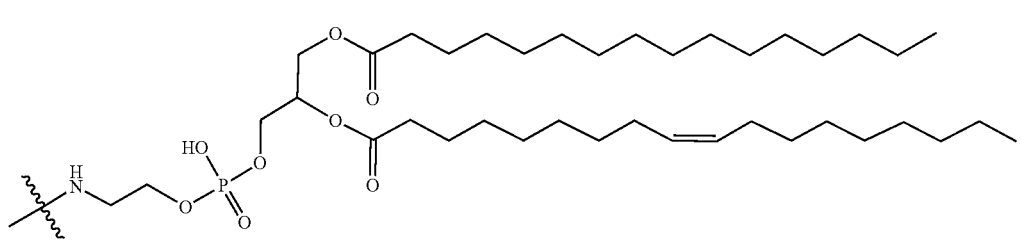
(XVIII)
[Chem. 17]
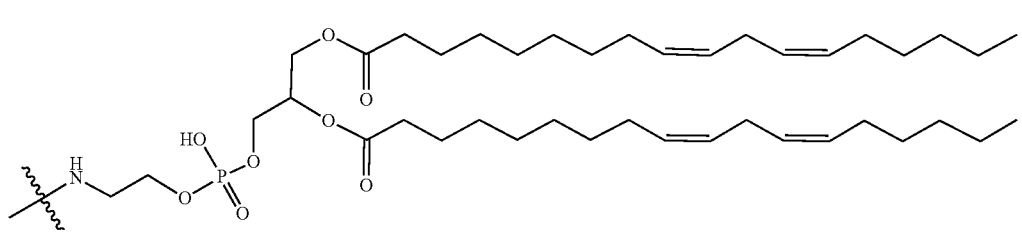
(XIX)
[Chem. 18]
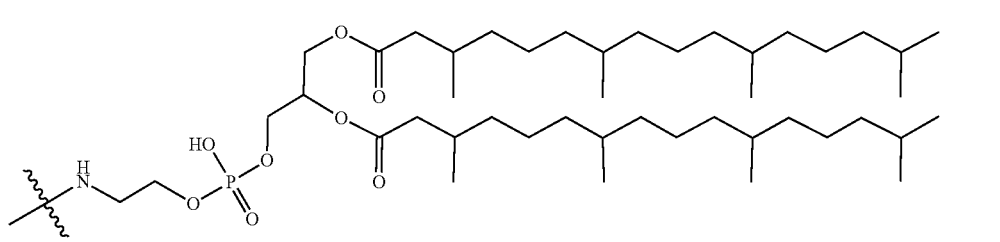
(XX)
[Chem. 19]
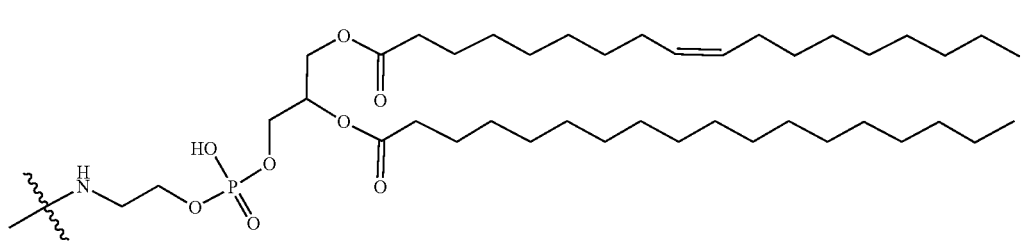
(XXI)
[Chem. 20]
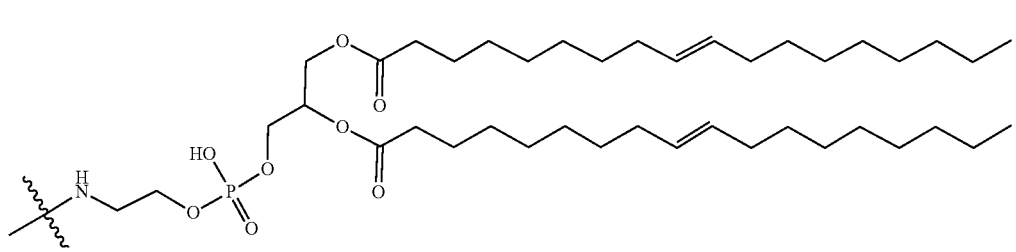
(XXII)

Herein, an "analog" refers to a compound having the same or similar basic backbone and having a similar structure and character. An analog comprises, for example, a biosynthetic intermediate, metabolite, and the like. A person skilled in the art can determine whether a compound is an analog of another compound. A person skilled in the art can produce a PE or analog thereof using a per se known method.

The second nucleic acid strand comprises 1 or more PEs or analogs thereof. If the second nucleic acid strand comprises a single PE or an analog thereof, the PE or an analog thereof is linked to the 5' end or 3' end of the second nucleic acid strand or a nucleotide at the inside of the second nucleic acid strand. Linked to the 5' end or 3' end is preferable. Furthermore, if the second nucleic acid strand comprises 2 or more PEs and/or analogs thereof, these may be linked to a plurality of positions of the second nucleic acid strand, and/or may be linked as one group to one position of the second nucleic acid strand. Each one of them is preferably linked to the 5' end and 3' end of the second nucleic acid strand, respectively.

The bond between the second nucleic acid strand and a PE or an analog thereof may be a direct binding or an indirect binding. Direct binding refers to a manner in which two molecules are directly bound. Indirect binding refers to a manner in which two molecules to be bound are bound via another substance.

In one embodiment, the second nucleic acid strand and a PE and/or an analog thereof may be bound via a phosphoric acid ester bond or a phosphorothioate bond to the 5' end or 3' end of the second nucleic acid strand or a nucleotide at the inside of the second nucleic acid strand.

In one embodiment, the binding to the 5' end of the second nucleic acid strand is via a phosphoric acid ester bond or a phosphorothioate bond.

In one embodiment, the binding to the 5' end of the second nucleic acid strand is via a phosphoric acid ester bond.

[Chem. 21]

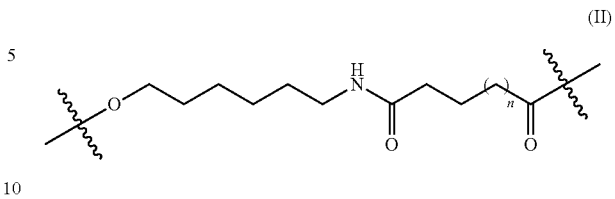

(II)

wherein n represents 0 or 1.

If the second nucleic acid strand and a PE or an analog thereof are indirectly bound, both may be bound via a cleavable linker. A "cleavable linker" refers to a linking group that can be cleaved under the physiological condition, for example, in the cell or in the animal body (for example, in the human body). The cleavable linker may be selectively cleaved with the endogenous enzyme such as nuclease or peptidase, the acidic conditions, the reductive environment, and the like. A specific example of such bond comprises, for example, an amide bond, ester bond, phosphoric acid ester bond, single or both ester bonds of a phosphodiester bond, carbamate bond, and disulfide bond, and a nucleotide linker such as a natural DNA linker.

In contrast, if the second nucleic acid strand and a PE or an analog thereof are indirectly bound, both may be bound via an uncleavable linker. An "uncleavable linker" refers to a linking group that cannot be cleaved under the physiological condition. Such uncleavable linker comprises, for example, a linker consisting of and a modified or unmodified deoxyribonucleoside or a modified or unmodified ribonucleoside linked by the phosphorothioate bond, and a phosphorothioate bond; and the like.

In one embodiment, if the second nucleic acid strand and a PE or an analog thereof are indirectly bound, the PE group bound to the linker is represented by the following general formula IV.

[Chem. 22]

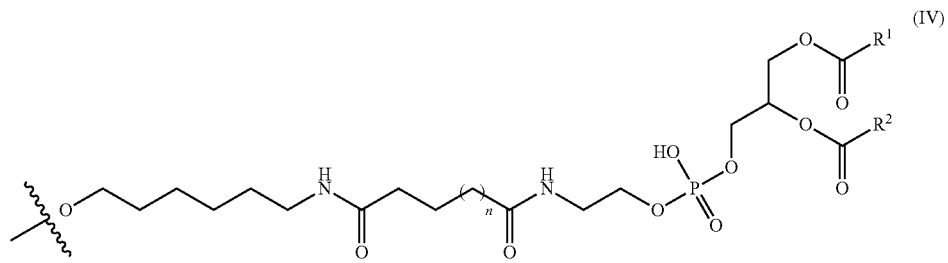

(IV)

If the second nucleic acid strand and a PE or an analog thereof are indirectly bound, the bond may be via a linking group (hereinafter, frequently referred to as a "linker"). A linker may be bound to the 5' end or 3' end of the second nucleic acid strand or a nucleotide at the inside of the second nucleic acid strand via a phosphoric acid ester bond or a phosphorothioate bond.

In one embodiment, a linker is bound to the 5' end of the second nucleic acid strand via a phosphoric acid ester bond or a phosphorothioate bond.

In one embodiment, a linker is bound to the 5' end of the second nucleic acid strand via a phosphoric acid ester bond.

A specific example of the linker comprises a linker represented by the following general formula II.

wherein $R^1$ and $R^2$ have the same meaning as $R^1$ and $R^2$ in the general formula I respectively, and n has the same meaning as n in the general formula II.

The second nucleic acid strand and a group represented by the general formula IV may be bound via a phosphoric acid ester bond or a phosphorothioate bond to the 5' end or 3' end of the second nucleic acid strand or a nucleotide at the inside of the second nucleic acid strand.

In one embodiment, a group represented by the general formula IV is bound to the 5' end of the second nucleic acid strand via a phosphoric acid ester bond or a phosphorothioate bond.

In one embodiment, a group represented by the general formula IV is bound to the 5' end of the second nucleic acid strand via a phosphoric acid ester bond.

In one embodiment, if a PE or an analog thereof is indirectly bound to the 5' end of the second nucleic acid strand, the PE group bound to the linker is represented by the following general formula III.

[Chem. 23]

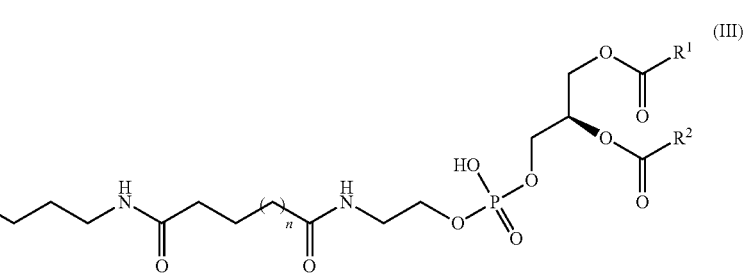

wherein the 5' oligo represents the 5' end of the oligonucleotide bound to the PE group. $R^1$ and $R^2$ have the same meaning as $R^1$ and $R^2$ in the general formula I respectively, and n has the same meaning as n in the general formula II.

If the linker is a nucleic acid such as DNA, or an oligonucleotide, a strand length of the cleavable linker or uncleavable linker may usually has, without particular limitation, a strand length of 1 to 20 bases, a strand length of 1 to 10 bases, or a strand length of 1 to 6 bases.

In certain embodiment, if a nucleic acid complex according to the present invention contains an optical isomer, stereoisomer, regioisomer, or rotational isomer, these are also comprised in the nucleic acid complex according to the present invention, and can each be obtained alone by a per se known synthesis method or separation method. For example, if an optical isomer is present in a nucleic acid complex according to the present invention, the optical isomer split from the compound is also encompassed in the nucleic acid complex according to the present invention.

In certain embodiment, a nucleic acid complex according to the present invention comprises a prodrug or a pharmaceutically acceptable salt of the prodrug. A prodrug and a pharmaceutically acceptable salt of the prodrug in a nucleic acid complex according to the present invention refer to a compound that is converted into a nucleic acid complex according to the present invention through reaction with an enzyme, gastric acid, or the like under the physiological condition in vivo, in other words, a compound that is changed to a nucleic acid complex according to the present invention by enzymically causing oxidation, reduction, hydrolysis, and the like or a compound that is changed to a nucleic acid complex according to the present invention by causing hydrolysis and the like with gastric acid or the like. In certain embodiment, a prodrug in a nucleic acid complex according to the present invention comprises 1 or more PEs or analogs thereof bound to the first nucleic acid strand or the second nucleic acid strand.

It was not known in the art that, as with a nucleic acid complex according to the present invention, binding a PE or an analog thereof to an end of the second nucleic acid strand of a double-stranded nucleic acid complex allows the double-stranded nucleic acid complex to permeate the blood brain barrier (BBB), increasing the efficiency of delivery to the central nervous system such as the brain. The present invention is based on such unexpected discovery.

An antisense effect that the first nucleic acid strand in a nucleic acid complex according to the present invention has on a target transcription product can be measured by a method known in the art. For example, after a nucleic acid complex according to the present invention is introduced in a cell and the like, a measurement can be performed using a known technology such as Northern blotting, quantitative PCR, or Western blotting. Specifically, it is possible to use the aforementioned known technology to verify that the antisense effect decreases the expression amount of a target gene or the level of a target transcription product (for example, the amount of mRNA or the amount of RNA such as microRNA, the amount of cDNA, the amount of protein, and the like) in a cell.

Measurement of the antisense effect of a nucleic acid complex according to the present invention in the central nervous system and determination of permeation through the blood brain barrier can also be measured by a method known in the art. Without limitation, for example, the determination can be done by measuring whether the expression amount of a target gene or the level of a target transcription product in the central nervous system is suppressed, several days to several months after (for example, 2 to 7 days after or 1 month after) an administration of a nucleic acid complex according to the present invention to a subject (for example, a mouse). As a criterion for the determination, it is possible to determine that the nucleic acid complex according to the present invention has permeated the blood brain barrier and provided an antisense effect in the central nervous system, if a measured value of the expression amount of the target gene or the level of the target transcription product is reduced for at least 5%, at least 10%, at least 15%, at least 20%, at least 25%, at least 30%, or at least 40% compared to a measured value of a negative control (for example, a vehicle administration). Further, the determination of blood brain barrier permeation can be done by measuring the amount (concentration) of the nucleic acid complex according to the present invention in the central nervous system, several days to several months after (for example, 2 to 7 days after or 1 month after) an administration of a nucleic acid complex according to the present invention to a subject (for example, a mouse).

As mentioned above, exemplary embodiments of a nucleic acid complex according to the present invention have been described, but the nucleic acid complex according to the present invention is not limited to the exemplary embodiments mentioned above. Furthermore, a person skilled in the art can produce, through selecting a known method suitably, a first nucleic acid strand and a second nucleic acid strand that are to be constituted with a nucleic acid complex according to the present invention in various embodiments. For example, a nucleic acid molecule according to the present invention can be produced by designing each nucleic acid molecule based on information on the base sequence of a target transcription product (for example, the base sequence of a target gene), synthesizing a nucleic acid using a commercially available automated nucleic acid synthesizer such as from, for example, GE Healthcare Inc., Thermo Fisher Scientific Inc., Beckman Coulter Inc., or the like, and then, purifying the resulting oligonucleotide using a reversed phase column or the like.

In one embodiment, a nucleic acid complex according to the present invention bound to a functional portion can be produced by using nucleic acid species already bound to a functional portion and performing the synthesis, purification, and annealing mentioned above. For example, the second nucleic acid strand may be produced by performing the synthesis and purification mentioned above using the nucleic acid species already bound to a PE or an analog thereof.

In one embodiment, a PE or an analog thereof can be bound, by a per se known method, to the second nucleic acid strand produced by performing the synthesis and purification mentioned above. Methods for linking a functional portion to a nucleic acid are well known in the art. A nucleic acid produced in this method is mixed in a suitable buffer solution and denatured at about 90° C. to 98° C. for several minutes (for example, 5 minutes), the nucleic acid is then annealed at about 30° C. to 70° C. for about 1 to 8 hours, so that one of the nucleic acid complexes according to the present invention. Alternatively, a nucleic acid strand is available by ordering from various manufacturers (for example, GeneDesign Inc.) with the base sequence and the site and kind of modification specified. The annealing step mentioned above can be done by leave the nucleic acid at room temperature (about 10° C. to about 35° C.) for about 5 to 60 minutes.

In some of the embodiments, a nucleic acid complex according to the present invention may be prepared in a manner in which each of the first nucleic acid strand and the second nucleic acid strand is dissolved in a buffer (for example, phosphate buffered saline) or water at about 70° C. to 98° C., the resulting two solutions are mixed, the solution mixture is retained at about 70° C. to 98° C. for several minutes (for example, 5 minutes), and then, the solution mixture is retained at about 30° C. to 70° C. (or 30° C. to 50° C.) for about 1 to 8 hours. Each of the first nucleic acid strand and the second nucleic acid strand can also be dissolved in a buffer (for example, phosphate buffered saline) or water at room temperature (about 10° C. to about 35° C.).

However, the condition (time and temperature) for annealing in production of a nucleic acid complex according to the present invention are not limited to the conditions mentioned above. Furthermore, conditions suitable to promote annealing of nucleic acid strands are well known in the art.

The present disclosure provides the following non-limiting embodiments.

Embodiment 1

A nucleic acid complex or a salt thereof comprising a first nucleic acid strand and a second nucleic acid strand,
wherein the first nucleic acid strand comprises a base sequence capable of hybridizing with at least part of a target transcription product and has an antisense effect on the target transcription product;
wherein the second nucleic acid strand comprises a base sequence complementary to the first nucleic acid strand and is bound to a phosphatidylethanolamine or an analog thereof; and
wherein the first nucleic acid strand is annealed to the second nucleic acid strand.

Embodiment 2

A nucleic acid complex or a salt thereof comprising a first nucleic acid strand and a second nucleic acid strand,
wherein the first nucleic acid strand
(1) comprises a base sequence having a length of 13 to 20 bases,
(2) is capable of hybridizing with at least part of a target transcription product,
(3) comprises at least 4 consecutive deoxyribonucleosides, and
(4) has an antisense effect on the target transcription product;
wherein the second nucleic acid strand
(1) comprises at least 4 consecutive ribonucleosides complementary to the at least 4 consecutive deoxyribonucleosides in the first nucleic acid strand, and
(2) is bound to a phosphatidylethanolamine or an analog thereof represented by the general formula I (preferably the general formula XV to XXII); and
wherein the first nucleic acid strand is annealed to the second nucleic acid strand.

Embodiment 3

A nucleic acid complex or a salt thereof comprising a first nucleic acid strand and a second nucleic acid strand,
wherein the first nucleic acid strand
(1) comprises a nucleoside and optionally an unnatural nucleoside, wherein the total number of the nucleoside(s) and the optionally comprised unnatural nucleoside(s) in the nucleic acid strand is 13 to 20,
(2) is capable of hybridizing with at least part of a target transcription product,
(3) comprises at least 4 consecutive deoxyribonucleosides that are recognized by RNase H,
(4) comprises unnatural nucleosides that are 1 or plural sugar-modified nucleotides located at the 5' and/or 3' side of the 4 consecutive nucleosides, and
(5) has an antisense effect on the target transcription product;
wherein the second nucleic acid strand
(1) comprises at least 4 consecutive ribonucleosides complementary to the at least 4 consecutive deoxyribonucleosides in the first nucleic acid strand,
(2) comprises 1 or more unnatural nucleosides located at the 5' side of the at least 4 consecutive ribonucleosides,
(3) comprises 1 or more unnatural nucleosides located at the 3' side of the at least 4 consecutive ribonucleosides, and
(4) is bound to a phosphatidylethanolamine or an analog thereof represented by the general formula I (preferably the general formula XV to XXII); and
wherein the first nucleic acid strand is annealed to the second nucleic acid strand.

Embodiment 4

A nucleic acid complex or a salt thereof comprising a first nucleic acid strand and a second nucleic acid strand,
wherein the first nucleic acid strand
(1) comprises a nucleoside and optionally an unnatural nucleoside, wherein the total number of the nucleosides and the optionally comprised unnatural nucleosides in the nucleic acid strand is 13 to 20, (2) is capable of hybridizing with at least part of a target transcription product, (3) comprises at least 4 consecutive deoxyribonucleosides that are recognized by RNase H, (4) comprises an unnatural nucleosides that are 1 or plural sugar-modified nucleotides located at the 5' and/or 3' side of the 4 consecutive nucleosides, and (5) has an antisense effect on the target transcription product;

wherein the second nucleic acid strand (1) comprises at least 4 consecutive ribonucleosides complementary to the at least 4 consecutive deoxyribonucleosides in the first nucleic acid strand, (2) comprises 1 or more unnatural nucleosides located at the 5' side of the at least 4 consecutive ribonucleosides, (3) comprises 1 or more unnatural nucleosides located at the 3' side of the at least 4 consecutive ribonucleosides, (4) is bound to a phosphatidylethanolamine or an analog thereof represented by the general formula I (preferably the general formula XV to XXII), and (5) wherein the second nucleic acid strand is bound to a phosphatidylethanolamine or an analog thereof (preferably at the 5' end of the second nucleic acid strand) via a linker represented by the general formula II; and wherein the first nucleic acid strand is annealed to the second nucleic acid strand.

Effect of Nucleic Acid Complex

A nucleic acid complex according to the present invention can inhibit the effect of a target miRNA in the central nervous system of a test subject. A specific example comprises a nucleic acid complex in which the first nucleic acid strand comprises a base sequence capable of hybridizing with at least part of a target miRNA and has an antisense effect on the target miRNA, and the second nucleic acid strand comprises a base sequence complementary to the first nucleic acid strand and is bound to a PE or an analog thereof, and in which the first nucleic acid strand and the second nucleic acid strand are annealed to each other. Inhibiting the effect of a target miRNA with this nucleic acid complex, the expression of a gene that is usually down-regulated by the target miRNA can be up-regulated.

A nucleic acid complex according to the present invention can regulate expression or editing of a target RNA in the central nervous system of a test subject. A specific example comprises a nucleic acid complex in which the first nucleic acid strand comprises a base sequence capable of hybridizing with at least part of a target RNA and has an antisense effect on the target RNA, and the second nucleic acid strand comprises a base sequence complementary to the first nucleic acid strand and is bound to a PE or an analog thereof, and in which the first nucleic acid strand and the second nucleic acid strand are annealed to each other. Here, "regulating expression of a target RNA" comprises, for example, up-regulation and down-regulation of the expression amount. Additionally, "regulating editing of a target RNA" comprises regulation of splicing by RNA editing, such as exon skipping or exon inclusion. A target RNA may be an RNA of a virus or bacteria or a toxic RNA.

A nucleic acid complex according to the present invention can inhibit translation of a target mRNA in the central nervous system of a test subject. A specific example comprises a nucleic acid complex in which the first nucleic acid strand comprises a base sequence capable of hybridizing with at least part of a target mRNA and has an antisense effect on the target mRNA, and the second nucleic acid strand comprises a base sequence complementary to the first nucleic acid strand and is bound to a PE or an analog thereof, and in which the first nucleic acid strand and the second nucleic acid strand are annealed to each other. Binding the first nucleic acid strand to a target mRNA with this nucleic acid complex, a steric block being generated, translation of the mRNA is inhibited.

Composition

A second aspect of the present invention is a composition. A composition according to the present invention comprises a nucleic acid complex according to the first aspect of the present invention as an active ingredient and/or as a drug delivery molecule. The nucleic acid complex according to the first aspect of the present invention permeates the BBB and can regulate the expression amount (for example, can reduce the expression amount) of a target transcription product in the central nervous system by an antisense effect. Therefore, a composition according to the present invention may be a pharmaceutical composition, or a composition to treat a test subject that is administered to a test subject so that the nucleic acid complex according to the present invention is delivered.

Furthermore, one embodiment of the present invention relates to a therapeutic method in which a composition containing a nucleic acid complex according to the present invention is administered so that each central nervous system disease is treated.

Formulation

Herein, the composition can be formulated using a per se known method. For example, the present composition can be used orally or parenterally in the form of a capsule, tablet, pill, liquid, powder, granule, microgranule, film coated agent, pellet, troche, sublingual agent, peptizer, buccal, paste, syrup, suspension, elixir, emulsion, coating agent, ointment, plaster, cataplasm, transdermal agent, lotion, inhalant, aerosol, eyedrop, injection solution, and suppository.

With regard to formulating these formulations, a pharmaceutically acceptable carrier or solvent or an acceptable carrier or solvent as a food and beverage can be suitably included. Specifically, such a carrier or solvent comprises sterile water, physiological saline, vegetable oil, a base, emulsifying agent, suspending agent, surfactant, pH adjustor, stabilizer, flavoring agent, perfume, excipient, vehicle, antiseptic, binding agent, diluent, isotonizing agent, sedative, extender, disintegrator, buffer, coating agent, lubricant, coloring agent, sweetener, thickener, flavoring agent, dissolving auxiliary, and other additive.

Form of Administration and Dose

Herein, there is no particular limitation about a preferable form of administration of the composition. For example, it may be oral administration or parenteral administration. A specific example of parenteral administration comprises intravenous administration, intraarterial administration, intraperitoneal administration, subcutaneously administration, intradermal administration, tracheal/bronchial administration, rectal administration, and intramuscular administration, and administration by transfusion. Administration can be done by intramuscular injection administration, intravenous infusion administration, or implantable type continuous subcutaneous administration. Subcutaneous administration is preferable, since it can be done as self-injection by patients themselves. Additionally, in intravenous administration, the amount of the nucleic acid complex according to the present invention contained in one dose of the composition, in other words, a single dose of the nucleic acid complex according to the present invention can be, for example, 0.001 mg/kg or more, 0.005 mg/kg or more, 0.01 mg/kg or more, 00.25 mg/kg or more, 0.5 mg/kg or more, 1 mg/kg or more, 2.5 mg/kg or more, 5 mg/kg or more, 10 mg/kg or more, 20 mg/kg or more, 30 mg/kg or more, 40 mg/kg or more, 50 mg/kg or more, 75 mg/kg or more, 100 mg/kg or more, 150 mg/kg or more, 200 mg/kg or more, 300 mg/kg or more, 400 mg/kg or more, or 500 mg/kg or more. For example, any amount included in the range of 0.001 mg/kg to 500 mg/kg (for example, 0.001 mg/kg, 0.01 mg/kg, 0.1 mg/kg, 1 mg/kg, 5 mg/kg, 10 mg/kg, 50 mg/kg, 100 mg/kg, or 200 mg/kg) can be suitably selected.

Test Subject, or Target to Be Applied

As used herein, a "test subject" refers to a subject to which a composition according to the present invention is applied. A test subject comprises not only an individual but also an organ, tissue, and cell. If a test subject is an individual, the composition according to the present invention can be applied for any animal, including a human. As a test target other than human, the test subject to be applied can be, for example, a various domestic animal, domestic fowl, pet animal, laboratory animal, and the like. A test subject may be an individual of which the expression amount of a target transcription product needs to be reduced in the central nervous system, or an individual which needs treatment of a central nervous system disease.

A composition according to the present invention can reduce the expression amount of a target transcription product in the central nervous system by the BBB permeation action and antisense effect of a nucleic acid complex according to the first aspect of the present invention encompassed in the composition.

If a composition according to the present invention is applied for the treatment of a central nervous system disease, a target disease to be applied is preferably a central nervous system disease associated with an increase or reduction in gene expression, in particular, a disease (tumor and the like) associated with an increase in expression of a target transcription product or a target gene. For example, it comprises, but are not limited to, brain tumor, Alzheimer's disease, Parkinson's disease, amyotrophic lateral sclerosis, multiple sclerosis, Huntington's disease, and the like.

A delivery site for a composition according to the present invention, more specifically, a delivery site for an active ingredinet contained in the composition is not particularly limited, but delivery to a suitable site according to each disease may allow to obtain an effective result. In treatment of Alzheimer's disease, as a specific example, drug delivery to the hippocampus and/or parietal lobe can be efficient. Additionally, in treatment of frontotemporal dementia (FTD) (including frontotemporal lobar degeneration (FTLD), semantic dementia (SD), progressive nonfluent aphasia (PNFA), and the like), and Pick disease, drug delivery to the frontal lobe, temporal lobe, and/or substantia nigra can be efficient. Furthermore, in treatment of Parkinson's disease dementia, drug delivery to the occipital lobe, substantia nigra, and/or striatum can be efficient. In addition, in treatment of Parkinson's disease, drug delivery to the substantia nigra and/or striatum can be efficient. In treatment of corticobasal degeneration (CBD), drug delivery to the frontal lobe, parietal lobe, basal ganglion, and/or substantia nigra can be efficient. In treatment of progressive supranuclear palsy (PSP), drug delivery to the frontal lobe, basal ganglion, and/or substantia nigra can be efficient. In treatment of amyotrophic lateral sclerosis, drug delivery to the frontal lobe, parietal lobe, basal ganglion, and/or substantia nigra can be efficient. In treatment of spinocerebellar degeneration (SCD) SCA type 1 to SCA type 34, drug delivery to the brainstem and/or cerebellum can be efficient. In treatment of dentato-rubro-pallido-luysian atrophy (DRPLA), drug delivery to the basal ganglion, brainstem, and/or cerebellum can be efficient. In treatment of spinobulbar muscular atrophy (SBMA), drug delivery to the brainstem and/or spinal cord can be efficient. In treatment of Friedreich's ataxia (FA), drug delivery to the brainstem and/or cerebellum can be efficient. In treatment of Huntington's disease, drug delivery to the striatum, frontal lobe, parietal lobe, and/or basal ganglion can be efficient. In treatment of prion disease (including bovine spongiform encephalopathy and GSS), drug delivery to the cerebral cortex, cerebral white matter, basal ganglion, and/or substantia nigra can be efficient. In treatment of cerebral white matter encephalopathy, drug delivery to the cerebral white matter can be efficient. In treatment of encephalitis (including viral, bacterial, mycotic, and tuberculous encephalitis) and meningitis (including viral, bacterial, mycotic, and tuberculous meningitis), drug delivery to the whole brain can be efficient. In treatment of metabolic encephalopathy, toxic encephalopathy, and trophic encephalopathy, drug delivery to the whole brain can be efficient. In treatment of cerebral white matter encephalopathy, drug delivery to the cerebral white matter can be efficient. In treatment of cerebral infarction, cerebral hemorrhage, subarachnoid hemorrhage, moyamoya disease, and cerebral anoxia, drug delivery to the whole brain can be efficient. In treatment of cerebral white matter encephalopathy, drug delivery to the cerebral white matter can be efficient. In treatment of diffuse axonal injury, drug delivery to the cerebral white matter can be efficient. In treatment of head injury, drug delivery to the whole brain can be efficient. In treatment of multiple sclerosis (MS) and neuromyelitis optica (NMO), drug delivery to the cerebral white matter, cerebral cortex, optic nerve, and/or spinal cord can be efficient. In treatment of myotonic dystrophy (DM1 and DM2), drug delivery to the skeletal muscle, myocardium, cerebral cortex, and/or cerebral white matter can be efficient. In treatment of familial spastic paraplegia (HSP), drug delivery to the parietal lobe and/or spinal cord can be efficient. In treatment of Fukuyama muscular dystrophy, drug delivery to the skeletal muscle, cerebral cortex, and/or cerebral white matter can be efficient. In treatment of dementia with Lewy body (DLB), drug delivery to the substantia nigra, striatum, occipital lobe, frontal lobe, and/or parietal lobe can be efficient. In treatment of multiple system atrophy (MSA), drug delivery to the striatum, basal ganglion, cerebellum, substantia nigra, frontal lobe, and/or temporal lobe can be efficient. In treatment of Alexander disease, drug delivery to the cerebral white matter can be efficient. In treatment of CADASIL and CARASIL, drug delivery to the cerebral white matter can be efficient.

If the composition is applied by administration or intake, the dose or amount of intake may be suitably selected in accordance with the age (including the age in month and the age in week), body weight, symptom, and health status of a test subject, the kind of the composition (pharmaceutical, food and beverage, and the like), and the like. The effective amount of a test subject's intake of a composition according to the present invention may be in amount, for example, such that a nucleic acid complex according to the present invention encompassed is 0.00001 mg/kg/day to 10000 mg/kg/day, or 0.001 mg/kg/day to 100 mg/kg/day. The composition may be administered for a single or multiple times. In administering multiple times, administration can be done each day or at suitable time intervals (for example, at intervals of 1 day, 2 days, 3 days, 1 week, 2 weeks, or 1 month), for example, for 2 to 20 times, and the like. One dose mentioned above of the nucleic acid complex according to the present invention can be, for example, 0.001 mg/kg or more, 0.005 mg/kg or more, 0.01 mg/kg or more, 00.25 mg/kg or more, 0.5 mg/kg or more, 1 mg/kg or more, 2.5 mg/kg or more, 0.5 mg/kg or more, 1.0 mg/kg or more, 2.0 mg/kg or more, 3.0 mg/kg or more, 4.0 mg/kg or more, 5 mg/kg or more, 10 mg/kg or more, 20 mg/kg or more, 30 mg/kg or more, 40 mg/kg or more, 50 mg/kg or more, 75 mg/kg or more, 100 mg/kg or more, 150 mg/kg or more, 200 mg/kg or more, 300 mg/kg or more, 400 mg/kg or more, or 500 mg/kg or more, and, for example, any dose included in the range of 0.001 mg/kg to 500 mg/kg (for example, 0.001 mg/kg, 0.01 mg/kg, 0.1 mg/kg, 1 mg/kg, 5 mg/kg, 10 mg/kg, 50 mg/kg, 100 mg/kg, or 200 mg/kg) can be suitably selected.

A nucleic acid complex according to the present invention may be administered at a dose of 0.01 to 10 mg/kg (for example, about 6.25 mg/kg) for 4 times at a frequency of twice per week. Furthermore, a nucleic acid complex according to the present invention may be administered at a dose of 0.05 to 30 mg/kg (for example, about 25 mg/kg) for 2 to 4 times at a frequency of once or twice per week, for example, for 2 times at a frequency of twice per week. Adopting such a dosage regimen (divided administration) makes it possible to reduce toxicity and decrease load to a test subject, compared to a single administration with a higher dose.

There is a limit (the upper limit) to the amount of BBB permeation and the amount of BNB permeation by a single administration of a nucleic acid complex according to the present invention, but the repeated administration is considered to allow the suppression effect to work additively in cells. In other words, in a high dose at the limit of BBB permeation and BNB permeation or higher (for example, 25 mg/kg or more), an increase in efficacy with the increase in a single dose is reduced, but repeated administration at certain intervals (for example, half a day or longer) are considered to be capable of enhancing efficacy.

In certain embodiment, a nucleic acid complex according to the present invention also has excellent pharmaceutical properties, such as excellent solubility in water, the second liquid for a dissolution test in The Japanese Pharmacopoeia, or the second liquid for a disintegration test in The Japanese Pharmacopoeia, excellent pharmacokinetics (e.g., drug half-life in blood, intracerebral transferability, metabolic stability, and CYP inhibition), low toxicity (better pharmaceutical property in terms of, for example, acute toxicity, chronic toxicity, genotoxicity, reproductive toxicity, cardiotoxicity, drug interaction, carcinogenicity, phototoxicity, and the like) and less side effects (for example, suppression of sedation).

Drug Delivery

Utilizing that a nucleic acid complex according to the first aspect of the present invention contained as an active ingredient to permeates the BBB and is delivered efficiently to the central nervous system, a composition according to the present invention allows to deliver a drug to the nervous system, particularly the central nervous system, by binding the specific drug to the first nucleic acid strand and/or the second nucleic acid strand. A drug to be delivered to the nervous system comprises, but not particularly limited to, a peptide, protein or nucleic acid drug, or other organic compounds, for example, a antitumor agent, hormone agent, antibiotic, antiviral agent, anti-inflammatory agent, and the like. Preferably, a drug is a small molecule drug. A "small molecule drug" is sufficiently understood in the art. A small molecule drug typically refers to a drug having a molecular weight of less than 1,000 daltons. A drug may be a lipophilic drug. A nucleic acid drug comprises, but is not particularly limited to, an ASO, antago-miR, splice-switching oligonucleotide, aptamer, single-stranded siRNA, microRNA, pre-microRNA, and the like. The binding position and kind of the bond of a drug in the second nucleic acid strand are as described above with reference to the bond between a phosphatidylethanolamine or an analog thereof and the second nucleic acid strand.

As disclosed in the following Examples, a composition according to the present invention can be highly efficiently delivered to the central nervous system, and can effectively alter or suppress the expression of a target gene or the level of a target transcription product. Accordingly, provided is a method of reducing the expression amount of a target transcription product in the central nervous system of a test subject, wherein administering a composition containing the nucleic acid complex according to the present invention to a test subject is comprised. The method may be a method of treating a central nervous system disease of a test subject. Furthermore, also provided is a method of drug delivery in which a drug is delivered to the central nervous system of a test subject, wherein administering a composition containing the nucleic acid complex according to the present invention to a test subject is comprised.

EXAMPLES

The present invention is explained in detail in the following by referring to Examples. However, the examples do not limit the present invention and the examples can be modified within the scope of the present invention.

"Room temperature" in the following Examples usually refers to about 10° C. to about 35° C. A ratio indicated for a solvent mixture refers to a volume ratio unless otherwise specified. Unless otherwise specified, % refers to wt. %.

When the description C18 is made in relation to preparative HPLC (high performance liquid chromatography), octadecyl-bonded silica gel was used. A ratio indicated for an elution solvent refers to a volume ratio unless otherwise specified.

The following abbreviations are used in the following Examples.

DIPEA: N,N-diisopropylethylamine
NMP: N-methyl-2-pyrrolidone
DMAP: 4-dimethylaminopyridine
HATU: O-(7-azabenzotriazole-1-yl)-N,N,N',N'-tetramethyluronium hexafluorophosphate salt
PBS: phosphate buffered saline
TEAA: triethylamine acetate
THF: tetrahydrofuran The structures of the oligonucleotides used in the following Examples are all listed in Table 1. Among the oligonucleotides used in Examples, ASO (Malat1) and HA-cRNA (Malat1) were synthesized by GeneDesign Inc. (Osaka, Japan).

TABLE 1

Oligonucleotides used in Examples

| Duplex Number | Double-Stranded Nucleic Acid Agent | Oligonucleotide | Sequence (from 5' to 3') | SEQ ID NO. |
|---|---|---|---|---|
| n/a | n/a | ASO (Malat1) | 5(L)^T(L)^A(L)^g^t^t^c^a^c^t^g^a^a^T(L)^G(L)^5(L) | 1 |
| n/a | n/a | HA-cRNA (Malat1) | HA-G(M)^C(M)^A(M)^UUCAGUGAAC^U(M)^A(M)^G(M) | 2 |
| n/a | n/a | Glutaryl-cRNA (Malat1) | Glutaryl-G(M)^C(M)^A(M)^UUCAGUGAAC^U(M)^A(M)^G(M) | 2 |
| 1 | DSPE-HDO | ASO (Malat1) | 5(L)^T(L)^A(L)^g^t^t^c^a^c^t^g^a^a^T(L)^G(L)^5(L) | 1 |
|  |  | DSPE-cRNA (Malat1) | DSPE-G(M)^C(M)^A(M)^UUCAGUGAAC^U(M)^A(M)^G(M) | 2 |
| 2 | DOPE-HDO | ASO (Malat1) | 5(L)^T(L)^A(L)^g^t^t^c^a^c^t^g^a^a^T(L)^G(L)^5(L) | 1 |
|  |  | DOPE-cRNA (Malat1) | DOPE-G(M)^C(M)^A(M)^UUCAGUGAAC^U(M)^A(M)^G(M) | 2 |
| 3 | DPPE-HDO | ASO (Malat1) | 5(L)^T(L)^A(L)^g^t^t^c^a^c^t^g^a^a^T(L)^G(L)^5(L) | 1 |
|  |  | DPPE-cRNA (Malat1) | DPPE-G(M)^C(M)^A(M)^UUCAGUGAAC^U(M)^A(M)^G(M) | 2 |
| 4 | POPE-HDO | ASO (Malat1) | 5(L)^T(L)^A(L)^g^t^t^c^a^c^t^g^a^a^T(L)^G(L)^5(L) | 1 |
|  |  | POPE-cRNA (Malat1) | POPE-G(M)^C(M)^A(M)^UUCAGUGAAC^U(M)^A(M)^G(M) | 2 |
| 5 | 18:1 (delta9-Trans) PE-HDO | ASO (Malat1) | 5(L)^T(L)^A(L)^g^t^t^c^a^c^t^g^a^a^T(L)^G(L)^5(L) | 1 |
|  |  | 18:1 (delta9-Trans) PE-cRNA (Malat1) | 18:1 (Δ9-Trans) PE-G(M)^C(M)^A(M)^UUCAGUGAAC^U(M)^A(M)^G(M) | 2 |
| 6 | 18:0-18:1 PE-HDO | ASO (Malat1) | 5(L)^T(L)^A(L)^g^t^t^c^a^c^t^g^a^a^T(L)^G(L)^5(L) | 1 |
|  |  | 18:0-18:1 PE-cRNA (Malat1) | 18:0-18:1 PE-G(M)^C(M)^A(M)^UUCAGUGAAC^U(M)^A(M)^G(M) | 2 |
| 7 | 18:2 PE-HDO | ASO (Malat1) | 5(L)^T(L)^A(L)^g^t^t^c^a^c^t^g^a^a^T(L)^G(L)^5(L) | 1 |
|  |  | 18:2 PE-cRNA (Malat1) | 18:2 PE-G(M)^C(M)^A(M)^UUCAGUGAAC^U(M)^A(M)^G(M) | 2 |
| 8 | DPyPE-HDO | ASO (Malat1) | 5(L)^T(L)^A(L)^g^t^t^c^a^c^t^g^a^a^T(L)^G(L)^5(L) | 1 |
|  |  | DPyPE-cRNA (Malat1) | DPyPE-G(M)^C(M)^A(M)^UUCAGUGAAC^U(M)^A(M)^G(M) | 2 |

Uppercase (L): LNA(5(L): 5-methylcytosine LNA),
Lowercase: DNA,
Uppercase: RNA,
Uppercase (M): 2'-OMe RNA,
^: phosphorothioate linkage The structure of HA described in Table 1 is represented by the following formula V:

[Chem. 24]

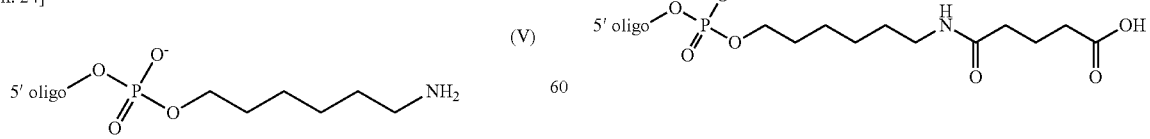

(V)

wherein "5' oligo" represents the 5' end of an oligonucleotide.

The structure of Glutaryl— described in Table 1 is represented by the following formula VI.

[Chem. 25]

(VI)

The structure of DSPE— described in Table 1 is represented by the following formula VII.

[Chem. 26]

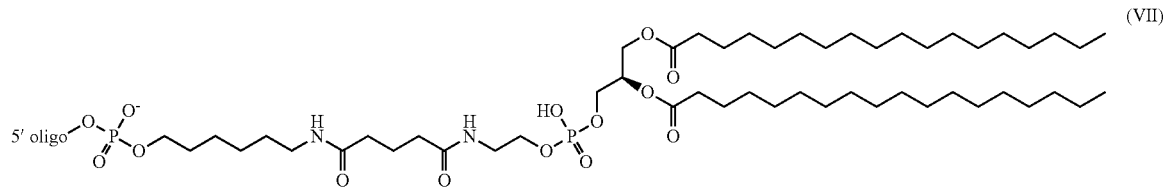
(VII)

wherein "5' oligo" represents the 5' end of an oligonucleotide.

The structure of DOPE—described in Table 1 is represented by the following formula VIII.

[Chem. 27]

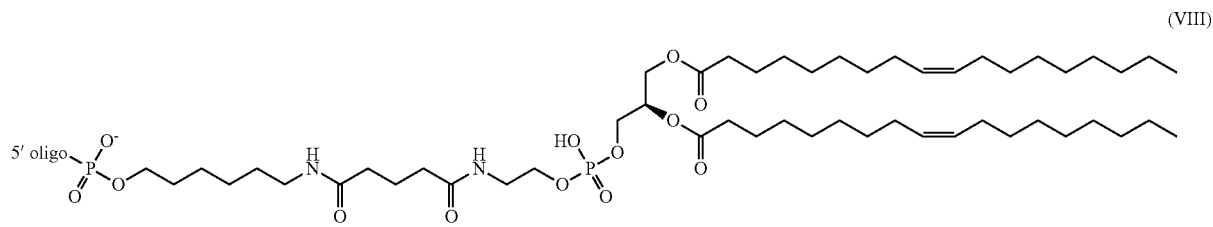
(VIII)

wherein "5' oligo" represents the 5' end of an oligonucleotide.

The structure of DPPE—described in Table 1 is represented by the following formula IX.

[Chem. 28]

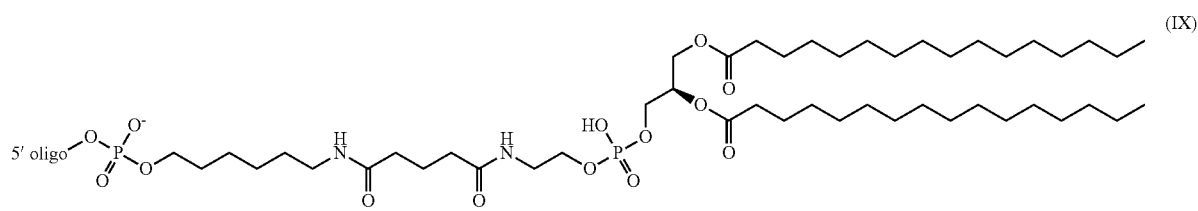
(IX)

wherein "5' oligo" represents the 5' end of an oligonucleotide.

The structure of POPE—described in Table 1 is represented by the following formula X.

[Chem. 29]

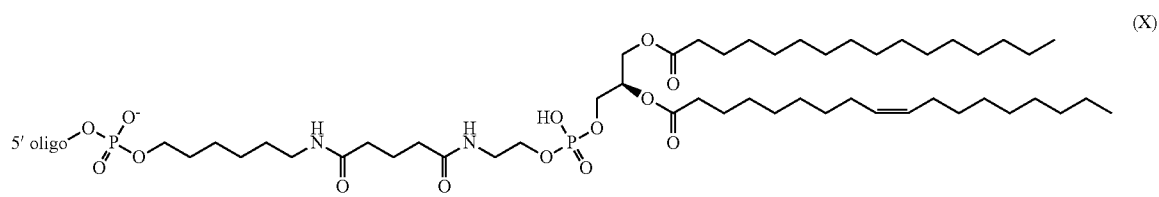
(X)

wherein "5' oligo" represents the 5' end of an oligonucleotide.

The structure of 18:1 (delta9-Trans) PE—described in Table 1 is represented by the following formula XI.

[Chem. 30]

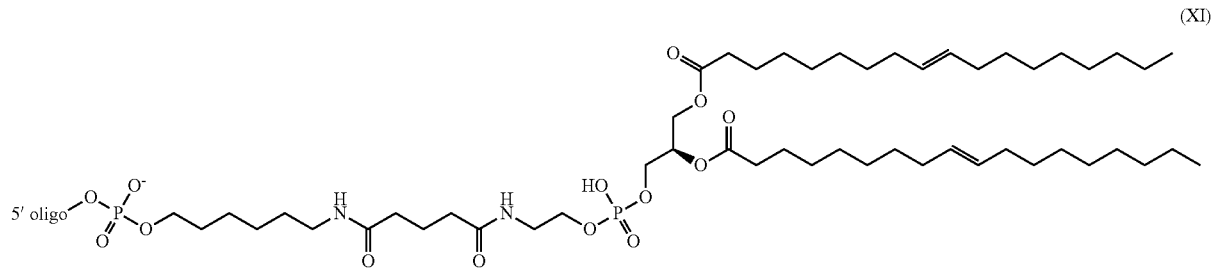

(XI)

wherein "5' oligo" represents the 5' end of an oligonucleotide.

The structure of 18:0-18:1 PE—described in Table 1 is represented by the following formula XII.

[Chem. 31]

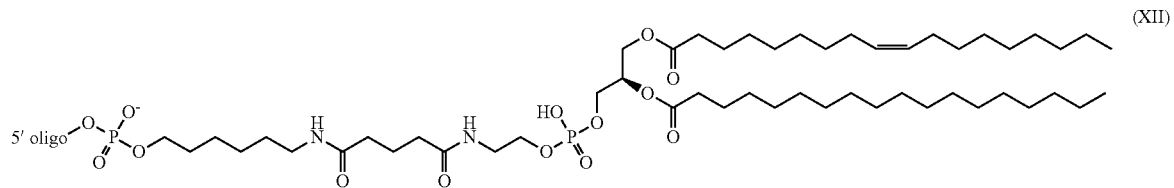

(XII)

wherein "5' oligo" represents the 5' end of an oligonucleotide.

The structure of 18:2 PE—described in Table 1 is represented by the following formula XIII.

[Chem. 32]

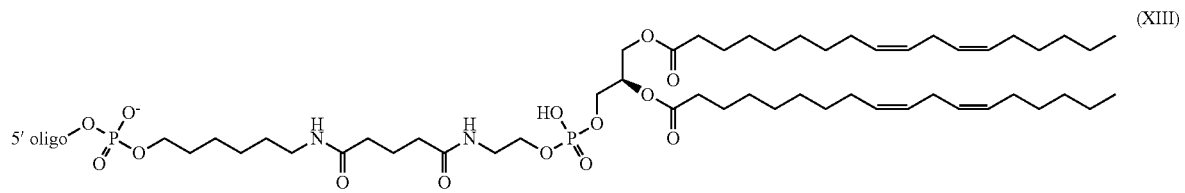

(XIII)

wherein "5' oligo" represents the 5' end of an oligonucleotide.

The structure of DPyPE—described in Table 1 is represented by the following formula XIV.

[Chem. 33]

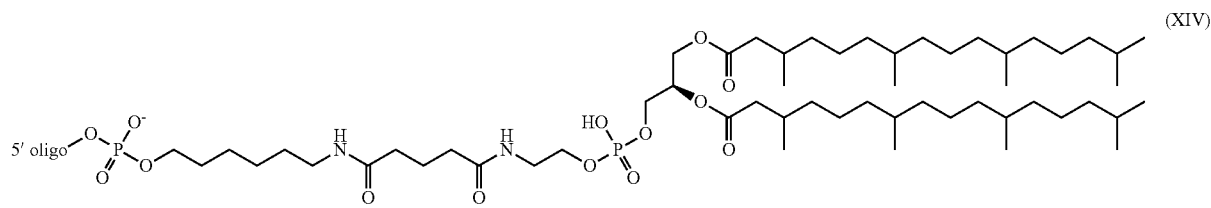

(XIV)

wherein "5' oligo" represents the 5' end of an oligonucleotide.

Example 1

(Step 1) Synthesis of DSPE-cRNA (Malat1)

The following procedure was used to synthesize a cRNA of a metastasis associated lung adenocarcinoma transcript (Malat1): (DSPE-cRNA (Malat1)) in which a 1,2-dstearoy-sn-glycero-1-phosphoethanolamine (1,2-Dioctadecanoyl-sn-glycero-3-phosphoethanolamine: DSPE) glutaryl group was bound to the 5' end. The ASO (Malat1) and the HA-cRNA (Malat1) were synthesized by GeneDesign, Inc. on consignment.

To an aqueous solution of the RNA strand (HA-cRNA (Malat1)) shown in Table 1 (4000 nmol), a 50 mM NMP solution of a commercially available COATSOME FE-8080SU5 (800 µL), distilled water (271 µL), NMP (7200 µL), ×10 PBS (1000 µL), and DIPEA (125 µL) were mixed in this order in an Eppendorf tube, and the resulting mixture was stirred, centrifuged, and then, allowed to react at 70° C. for 2 hours. The sample was solvent exchanged by gel filtration chromatography (Sephadex G-25; manufactured by GE Healthcare; mobile phase: distilled water) followed by lyophilization. The residue was purified by preparative HPLC (column: Xbridge OST C18 2.5 µm, 10 mm ID×50 mm; manufactured by Waters Corporation; mobile phase: TEAA/acetonitrile) and desalted by ultrafiltration (Amicon ultra; manufactured by Merck Millipore; distilled water). To the resulting solution (300 µL), 10 times the amount of 1 M meglumine acetate was added and well stirred, left for 5 minutes for ion exchange. Then, the desaltation was performed by ultrafiltration (Amicon ultra pore 3 kDa; manufactured by Merck Millipore; distilled water). The final product was filtrated through a 0.20 µm membrane filter and lyophilized to obtain 730 nmol of the compound in the title as a 5% dextrose solution.

(Step 2) Synthesis of Double-Stranded Nucleic Acid Agent DSPE-HDO

The ASO (Malat1) shown in Table 1 is a 16-mer single-stranded LNA/DNA gapmer targeted at an Malat1 non-coding RNA, comprising 3 LNA nucleosides at the 5' end, 3 LNA nucleosides at the 3' end and 10 DNA nucleosides between them. This LNA/DNA gapmer has a base sequence complementary to positions 1316 to 1331 of the Malat1 non-coding RNA (GenBank Accession No. NR_002847, SEQ ID NO: 3) of mouse.

Both nucleic acid strands: an ASO (Malat1) as the first nucleic acid strand; and the DSPE-cRNA (Malat1) obtained in Step 1 in Example 1 as the second nucleic acid strand, were mixed in equimolar amounts, and the resulting solution was heated at 70° C. for 7 minutes and slowly cooled to room temperature. In this manner, both nucleic acid strands were annealed to prepare a "DSPE glutaryl conjugated heteroduplex oligonucleotide (DSPE-conjugated heteroduplex oligonucleotide: DSPE-HDO)", a nucleic acid complex according to the present invention.

Example 2

(Step 1) Synthesis of DOPE-cRNA (Malat1)

The following procedure was used to synthesize a cRNA of an Mala1 (DOPE-cRNA (Malat1)) in which a 1,2-Dioleoyl-sn-glycero-3-phosphoethanolamine (1,2-Dioleoyl-sn-glycero-3-phosphatidylethanolamine: DOPE) glutaryl group was bound to the 5' end.

An aqueous solution (4000 nmol) of the RNA strand (HA-cRNA (Malat1)) shown in Table 1 was used in accordance with the same procedure as in Step 1 in Example 1 so that a DOPE-cRNA (Malat1) as a cRNA having a DOPE glutaryl group bound to the 5' end thereof was synthesized and obtained 1050 nmol thereof as a 5% dextrose solution.

(Step 2) Synthesis of Double-Stranded Nucleic Acid Agent DOPE-HDO

Both nucleic acid strands: an ASO (Malat1) as the first nucleic acid strand; and the DOPE-cRNA (Malat1) obtained in Step 1 in Example 2 as the second nucleic acid strand, were mixed in equimolar amounts, and, in the same manner as in Step 2 in Example 1, a "DOPE glutaryl conjugated heteroduplex oligonucleotide (DOPE-conjugated heteroduplex oligonucleotide: DOPE-HDO)", a nucleic acid complex according to the present invention was prepared.

Example 3

(Step 1) Synthesis of DPPE-cRNA (Malat1)

The following procedure was used to synthesize a cRNA of a Malat1 (DPPE-cRNA (Malat1)) in which a 1,2-dipalmitoyl-sn-glycero-3-phosphoethanolamine (DPPE) glutaryl group was bound to the 5' end.

An aqueous solution (5500 nmol) of the RNA strand (HA-cRNA (Malat1)) shown in Table 1 was used in accordance with the same procedure as in Step 1 in Example 1 so that a DPPE-cRNA (Malat1) as a cRNA having a DPPE glutaryl group bound to the 5' end thereof was synthesized and obtained 891 nmol thereof as a 5% dextrose solution.

(Step 2) Synthesis of Double-Stranded Nucleic Acid Agent DPPE-HDO

Both nucleic acid strands: an ASO (Malat1) as the first nucleic acid strand; and the DPPE-cRNA (Malat1) obtained in Step 1 in Example 3 as the second nucleic acid strand, were mixed in equimolar amounts, and, in the same manner as in Step 2 in Example 1, a "DPPE glutaryl conjugated heteroduplex oligonucleotide (DPPE-conjugated heteroduplex oligonucleotide: DPPE-HDO)", a nucleic acid complex according to the present invention was prepared.

Example 4

(Step 1) Synthesis of POPE-cRNA (Malat1)

The following procedure was used to synthesize a cRNA of a Malat1 (POPE-cRNA (Malat1)) in which a 1-palmitoyl-2-oleoyl-sn-glycero-3-phosphoethanolamine (POPE) glutaryl group was bound to the 5' end.

An aqueous solution (4000 nmol) of the RNA strand (HA-cRNA (Malat1)) shown in Table 1 was used in accordance with the same procedure as in Step 1 in Example 1 so that a POPE-cRNA (Malat1) as a cRNA having a POPE glutaryl group bound to the 5' end thereof was synthesized and obtained 579 nmol thereof as a 5% dextrose solution.

(Step 2) Synthesis of Double-Stranded Nucleic Acid Agent POPE-HDO

Both nucleic acid strands: an ASO (Malat1) as the first nucleic acid strand; and the POPE-cRNA (Malat1) obtained in Step 1 in Example 4 as the second nucleic acid strand, were mixed in equimolar amounts, and, in the same manner as in Step 2 in Example 1, a "POPE glutaryl conjugated heteroduplex oligonucleotide (POPE-conjugated heteroduplex oligonucleotide: POPE-HDO)" that is a nucleic acid complex according to the present invention was prepared.

Example 5

(Step 1) Synthesis of Glutaryl-cRNA (Malat1)

To an aqueous solution of the RNA strand (HA-cRNA (Malat1)) shown in Table 1 (5000 nmol), a 50 mM NMP solution of commercially available glutaric anhydride (2000 μL), distilled water (415 μL), NMP (6000 μL), ×10 PBS (1250 μL), and a 50 mM NMP solution of commercially available DMAP (2000 μL) were mixed in this order in an Eppendorf tube, and the resulting mixture was stirred, centrifuged, and then, allowed to react at 70° C. for 2 hours. The sample was solvent exchanged by gel filtration chromatography (Sephadex G-25; manufactured by GE Healthcare; mobile phase: distilled water) followed by lyophilization to obtain 4542 nmol of the compound in the title.

(Step 2) Synthesis of 18:1 (Delta9-Trans) PE-cRNA (Malat1)

The following procedure was used to synthesize a cRNA of an Malat1 (18:1 (delta9-Trans) PE-cRNA (Malat1)) in which a 1,2-dielaidoyl-sn-glycero-3-phosphoethanolamine (18:1 (delta9-Trans) PE) glutaryl group was bound to the 5' end.

To an aqueous solution of the RNA strand (Glutaryl-cRNA (Malat1)) synthesized in Step 1 in Example 5 (2300 nmol), a 25 mM NMP/THF solution (1:1 solution mixture) of commercially available 18:1 (delta9-Trans) PE (920 μL), distilled water (18 μL), NMP (1668 μL), THF (2128 μL), DIPEA (72 μL), and a 75 mM NMP solution of HATU (460 μL) were mixed in this order in an Eppendorf tube, and the resulting mixture was stirred, centrifuged, and then, allowed to react at 70° C. for 1 hour. The reaction solution was purified with an ODS column (column: Purif-Pack (registered trademark)-EX ODS-50, size 60; manufactured by Shoko Science Co., Ltd.; mobile phase: TEAA/acetonitrile) and desalted by ultrafiltration (Amicon ultra; manufactured by Merck Millipore; distilled water). To the resulting solution, 10 times the amount of 1 M meglumine acetate was added and well stirred, left for 5 minutes for ion exchange. Then, the desaltation was performed by ultrafiltration (Amicon ultra; manufactured by Merck Millipore; distilled water). The final product was filtrated through a 0.20 μm membrane filter and lyophilized to obtain 1071 nmol of the compound in the title.

(Step 3) Synthesis of Double-Stranded Nucleic Acid Agent 18:1 (Delta9-Trans) PE-HDO Both nucleic acid strands: an ASO (Malat1) as the first nucleic acid strand; and the 18:1 (delta9-Trans) PE-cRNA (Malat1) obtained in Step 2 in Example 5 as the second nucleic acid strand, were mixed in equimolar amounts, and, in the same manner as in Step 2 in Example 1, a "18:1 (delta9-Trans) PE glutaryl conjugated heteroduplex oligonucleotide (18:1 (delta9-Trans) PE-conjugated heteroduplex oligonucleotide: 18:1 (delta9-Trans) PE-HDO)" that is a nucleic acid complex according to the present invention was prepared.

Example 6

(Step 1) Synthesis of 18:0-18:1 PE-cRNA (Malat1)

The following procedure was used to synthesize a cRNA of a Malat1 (18:0-18:1 PE-cRNA (Malat1)) in which a 1-stearoyl-2-oleoyl-sn-glycero-3-phosphoethanolamine (18:0-18:1 PE) glutaryl group was bound to the 5' end.

An aqueous solution (2300 nmol) of the RNA strand (Glutaryl-cRNA(Malat1)) synthesized in the same manner as in Step 1 in Example 5 was used in accordance with the same procedure as in Step 2 in Example 5 so that a 18:0-18:1 PE-cRNA (Malat1) as a cRNA having a 18:0-18:1 PE glutaryl group bound to the 5' end thereof was synthesized and obtained 721 nmol thereof as a 5% dextrose solution.

(Step 2) Synthesis of Double-Stranded Nucleic Acid Agent 18:0-18:1 PE-HDO

Both nucleic acid strands: an ASO (Malat1) as the first nucleic acid strand; and the 18:0-18:1 PE-cRNA (Malat1) obtained in Step 1 in Example 6 as the second nucleic acid strand, were mixed in equimolar amounts, and, in the same manner as in Step 2 in Example 1, a "18:0-18:1 PE glutaryl conjugated heteroduplex oligonucleotide (18:0-18:1 PE-conjugated heteroduplex oligonucleotide: 18:0-18:1 PE-HDO)" that is a nucleic acid complex according to the present invention was prepared.

Example 7

(Step 1) Synthesis of 18:2 PE-cRNA (Malat1)

The following procedure was used to synthesize a cRNA of a Malat1 (18:2 PE-cRNA (Malat1)) in which a 1,2-dilinoleoyl-sn-glycero-3-phosphoethanolamine (18:2 PE) glutaryl group was bound to the 5' end.

An aqueous solution (2500 nmol) of the RNA strand (Glutaryl-cRNA(Malat1)) synthesized in the same manner as in Step 1 in Example 5 was used in accordance with the same procedure as in Step 2 in Example 5 so that a 18:2 PE-cRNA (Malat1) as a cRNA having a 18:2 PE glutaryl group bound to the 5' end thereof was synthesized and obtained 544 nmol thereof as a 5% dextrose solution.

(Step 2) Synthesis of Double-Stranded Nucleic Acid Agent 18:2 PE-HDO

Both nucleic acid strands: an ASO (Malat1) as the first nucleic acid strand; and the 18:2 PE-cRNA (Malat1) obtained in Step 1 in Example 7 as the second nucleic acid strand, were mixed in equimolar amounts, and, in the same manner as in Step 2 in Example 1, a "18:2 PE glutaryl conjugated heteroduplex oligonucleotide (18:2 PE-conjugated heteroduplex oligonucleotide: 18:2 PE-HDO)" that is a nucleic acid complex according to the present invention was prepared.

Example 8

(Step 1) Synthesis of DPyPE-cRNA (Malat1)

The following procedure was used to synthesize a cRNA of an Malat1 (DPyPE-cRNA (Malat1)) in which a 1,2-diphytanoyl-sn-glycero-3-phosphoethanolamine (DPyPE) glutaryl group was bound to the 5' end.

An aqueous solution (2400 nmol) of the RNA strand (Glutaryl-cRNA (Malat1)) synthesized in Step 1 in Example 5 was used in accordance with the same procedure as in Step 2 in Example 5 so that a DPyPE-cRNA (Malat1) as a cRNA having a DPyPE glutaryl group bound to the 5' end thereof was synthesized and obtained 961 nmol thereof as a 5% dextrose solution.

(Step 2) Synthesis of Double-Stranded Nucleic Acid Agent DPyPE-HDO

Both nucleic acid strands: an ASO (Malat1) as the first nucleic acid strand; and the DPyPE-cRNA (Malat1) obtained in Step 1 in Example 8 as the second nucleic acid strand, were mixed in equimolar amounts, and, in the same manner as in Step 2 in Example 1, a "DPyPE glutaryl conjugated heteroduplex oligonucleotide (DPyPE-conjugated heteroduplex oligonucleotide: DPyPE-HDO)" that is a nucleic acid complex according to the present invention was prepared.

Example 9

(A) In Vivo Experiment

The laboratory animal used was 7-week-old male mouse, C57BL/6J (Charles River Laboratories Japan, Inc.), and 2 mice per group were subjected to an experiment. For the experimental group, a solution containing a nucleic acid was intravenously administered once through the tail vein of the mouse at a dose of 5 mL/kg. For the comparative group, a solvent (5% dextrose solution) used to prepare a nucleic acid solution was intravenously administered to the mouse in accordance with the same procedure as for the experimental group.

(B) Analysis of Expression 72 hours after administering the nucleic acid solution, the mouse was anesthetized with 50 mg/kg of pentobarbital administered intraperitoneally, its blood was collected and was sacrificed, then the brain (cerebral hemisphere or cerebral cortex) was extracted. For extraction of the total RNA from the brain tissue, a reagent for RNA extraction, ISOGEN (Nippon Gene Co., Ltd.), was used. After the extracted brain tissue was disrupted in the ISOGEN solution, it was separated as a RNA fraction using chloroform. Then, a nucleic acid separation system, QuickGene RNA tissue kit SII (Kurabo Industries Ltd.), was used. For cDNA synthesis from the total RNA, ReverTra Ace qPCR RT Kit (Toyobo Co., Ltd.) was used, and quantitative PCR was performed with THUNDERBIRD qPCR Mix (Toyobo Co., Ltd.). For the quantitative PCR, a fluorescent probe method was adopted, and as the fluorescent probes, a mouse Malat1 (Integrated DNA Technologies, Inc.) and a mouse Gapdh (Thermo Fisher Scientific K.K.) were used. For the gene fragment amplification reaction condition for the quantitative PCR, the protocol of THUNDERBIRD qPCR Mix (Toyobo Co., Ltd.) mentioned above was followed. The expression amount of the mice Malat1 and Gapdh (the internal standard genes) were calculated using a relative calibration curve, and the relative expression level was calculated as Malat1/Gapdh. From the results of the 2 mice per group, the average value of the relative expression levels was calculated. Taken the average value of the relative expression levels for the comparative group as 100%, the ratio of the average value of the relative expression levels for the experimental group was calculated as a relative Malat1 ncRNA expression level.

(C) Results

The results of Example 9 are shown in Table 2. In the Table, the dose represents the amounts of ASO (Malat1).

Both the double-strand No. 1: DSPE-HDO and the double-strand No. 2: DOPE-HDO suppressed the expression of the Malat1 non-coding RNA in the cerebral cortex. Furthermore, all of the double-strand No. 3: DPPE-HDO, the double-strand No. 4: POPE-HDO, the double-strand No. 5: 18:1 (delta9-Trans) PE-HDO, the double-strand No. 6: 18:0-18:1 PE-HDO, the double-strand No. 7: 18:2 PE-HDO, and the double-strand No. 8: DPyPE-HDO suppressed the expression of the Malat1 non-coding RNA in the cerebral hemisphere. These results have proved that the double-stranded nucleic acid complex constituted with an ASO and a complementary strand to which a phosphatidylethanolamine or an analog thereof is bound can be delivered to the brain and provide an antisense effect there.

TABLE 2

Malat1 ncRNA Expression Inhibition Effect of Double Nucleic Acid Agent in Cerebral Cortex

| Duplex Number | Dose | Relative Malat1 ncRNA Expression Level |
|---|---|---|
| 1 | 50 mg/kg | 64% |
| 2 | 50 mg/kg | 76% |
| 3 | 50 mg/kg | 75% |
| 4 | 50 mg/kg | 74% |
| 5 | 50 mg/kg | 78% |
| 6 | 50 mg/kg | 79% |
| 7 | 50 mg/kg | 73% |
| 8 | 50 mg/kg | 67% |

All publications, patents, and patent applications cited herein are incorporated herein by reference in their entirety.

The invention claimed is:

1. A nucleic acid complex comprising a first nucleic acid strand and a second nucleic acid strand, wherein the first nucleic acid strand comprises a base sequence capable of hybridizing with at least part of a target transcription product and has an antisense effect on the target transcription product;

wherein half or less or none of the full length of the first nucleic acid strand is natural ribonucleosides, wherein the second nucleic acid strand comprises a base sequence complementary to the first nucleic acid strand and is bound to a phosphatidylethanolamine or an analog thereof;

wherein the phosphatidylethanolamine or an analog thereof is represented by the general formula I:

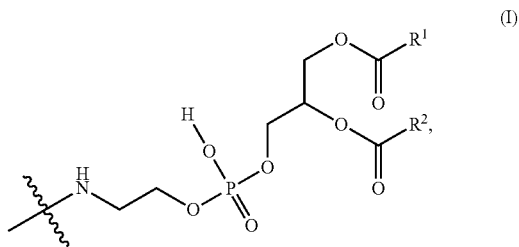

wherein $R^1$ and $R^2$ independently represent a substituted or unsubstituted $C_5$-$C_{32}$ alkyl group, or a substituted or unsubstituted $C_5$-$C_{32}$ alkenyl group, and wherein the first nucleic acid strand is annealed to the second nucleic acid strand.

2. The nucleic acid complex according to claim 1, wherein $R^1$ and $R^2$ independently represent a $C_{15}$-$C_{19}$ alkyl group, or a $C_{17}$ alkenyl group.
3. The nucleic acid complex according to claim 1, wherein the phosphatidylethanolamine or an analog thereof is represented by the general formulae XV to XXII:
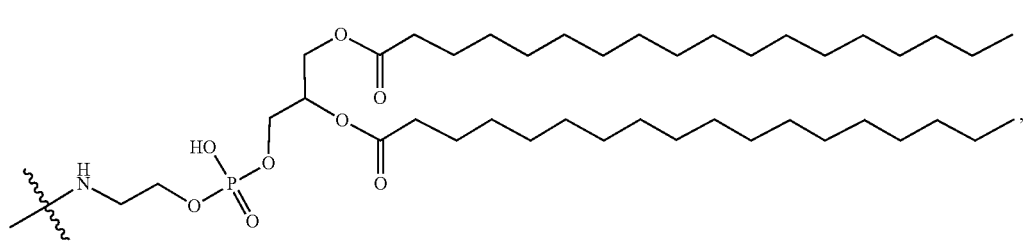
(XV)
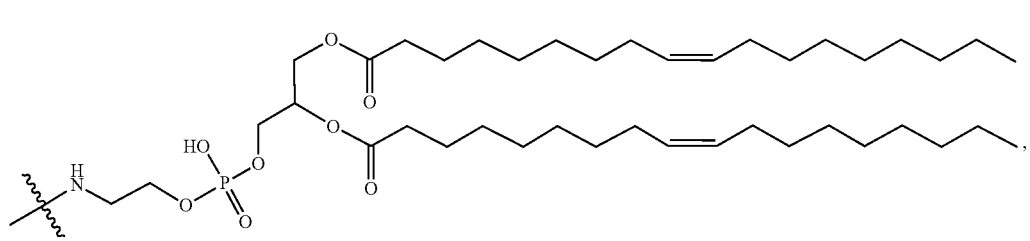
(XVI)
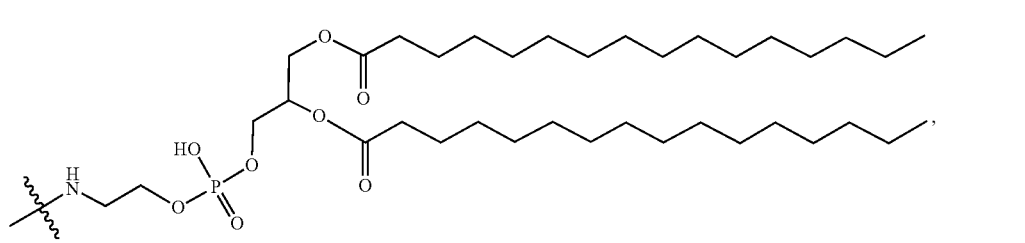
(XVII)
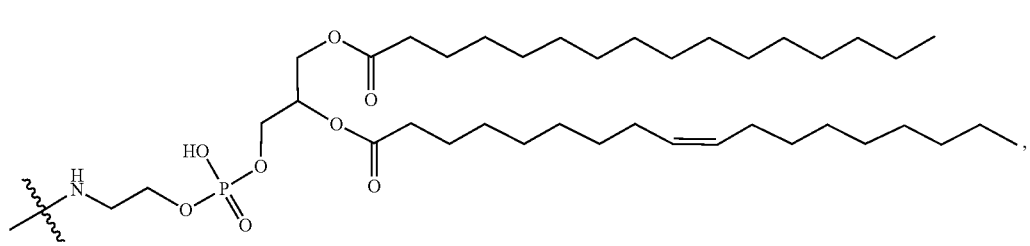
(XVIII)
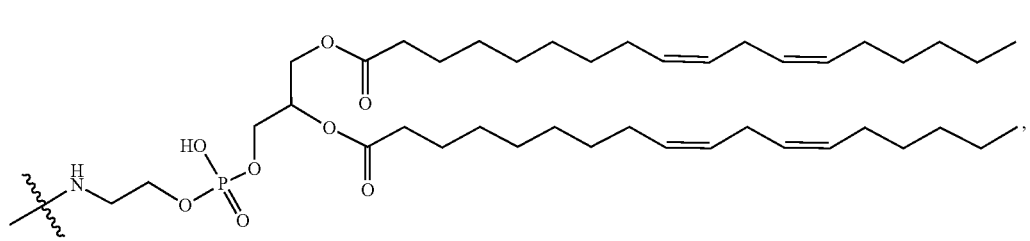
(XIX)
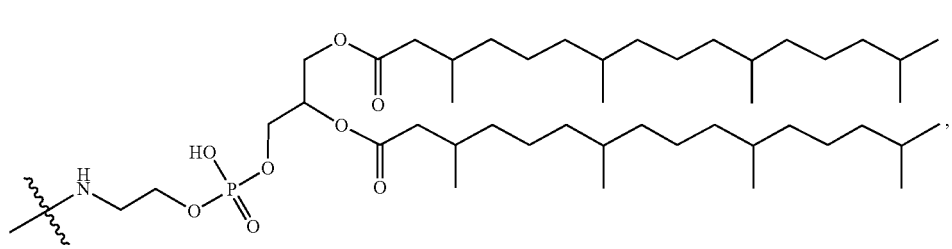
(XX)

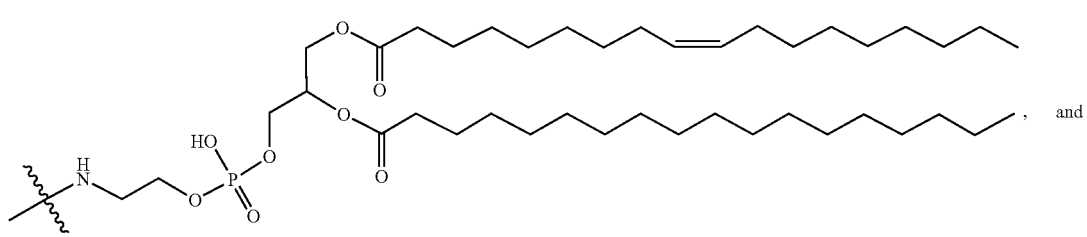
(XXI)

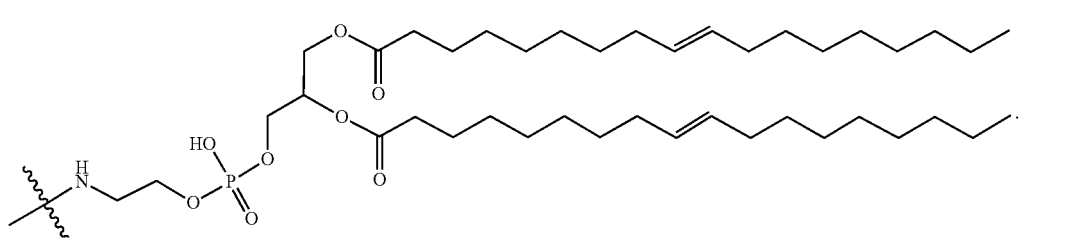
(XXII)

4. The nucleic acid complex according to claim 1, wherein the second nucleic acid strand is bound to a phosphatidylethanolamine or an analog thereof via a linker represented by the general formula II:

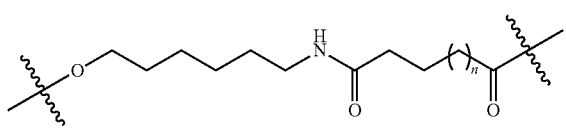
(II)

wherein n is 0 or 1.

5. The nucleic acid complex according to claim 4, wherein the 5' end of the second nucleic acid strand is bound to a phosphatidylethanolamine or an analog thereof via the linker.

6. The nucleic acid complex according to claim 1, wherein the first nucleic acid strand comprises at least 4 consecutive deoxyribonucleosides.

7. The nucleic acid complex according to claim 1, wherein the first nucleic acid strand is a gapmer.

8. The nucleic acid complex according to claim 6, wherein the second nucleic acid strand comprises at least 4 consecutive ribonucleosides complementary to the at least 4 consecutive deoxyribonucleosides in the first nucleic acid strand.

9. The nucleic acid complex according to claim 1, wherein the first nucleic acid strand is a mixmer.

10. The nucleic acid complex according to claim 1, wherein the first nucleic acid strand has a length of 13 to 20 bases.

11. The nucleic acid complex according to claim 1, wherein the second nucleic acid strand comprises no natural ribonucleoside.

12. The nucleic acid complex according to claim 1, wherein the nucleic acid portion of the second nucleic acid strand consists of deoxyribonucleosides and/or sugar-modified nucleosides, which are linked by modified or unmodified internucleoside bonds.

13. A method for regulating the expression or editing of a target transcription product in the central nervous system, comprising administering to a subject in need thereof a composition containing the nucleic acid complex according to claim 1.

14. The method according to claim 13, wherein said administering treats a central nervous system disease in the subject.

15. A method for delivering a central nervous system agent, comprising administering to a subject in need thereof a composition containing the nucleic acid complex according to claim 1.

16. The method according to claim 13, wherein the central nervous system is selected from the group consisting of cerebral cortex, basal ganglion, cerebral white matter, diencephalon, brainstem, cerebellum, and spinal cord.

17. The method according to claim 13, wherein the central nervous system is selected from the group consisting of frontal lobe, temporal lobe, hippocampus, parahippocampal gyms, parietal lobe, occipital lobe, striatum, globus pallidus, claustrum, thalamus, subthalamic nucleus, midbrain, substantia nigra, pons, medulla oblongata, cerebellar cortex, cerebellar nucleus, cervical spinal cord, thoracic spinal cord, and lumbar spinal cord.

18. The method according to claim 13, wherein said administering is intravenous administration or subcutaneous administration.

19. The method according to claim 13, wherein one dose of the administered composition contains 5 mg/kg or more of the nucleic acid complex.

20. The method according to claim 13, wherein upon said administering, the nucleic acid complex permeates blood brain barrier (BBB).

* * * * *